US010456441B2

(12) United States Patent
Budd et al.

(10) Patent No.: US 10,456,441 B2
(45) Date of Patent: Oct. 29, 2019

(54) AUGMENTING THE IMMUNE RESPONSE BY PROMOTING CELL DEATH OF IMMUNE CELLS

(71) Applicant: The University of Vermont and State Agricultural College, Burlington, VT (US)

(72) Inventors: Ralph C. Budd, Hinesburg, VT (US); Cheryl Collins, Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 15/892,280

(22) Filed: Feb. 8, 2018

(65) Prior Publication Data

US 2018/0169178 A1    Jun. 21, 2018

Related U.S. Application Data

(62) Division of application No. 14/806,047, filed on Jul. 22, 2015, now Pat. No. 9,925,230.

(60) Provisional application No. 62/027,641, filed on Jul. 22, 2014.

(51) Int. Cl.
| | | |
|---|---|---|
| *G01N 33/554* | (2006.01) | |
| *C07K 1/00* | (2006.01) | |
| *A61K 38/06* | (2006.01) | |
| *A61K 39/02* | (2006.01) | |
| *A61K 39/39* | (2006.01) | |
| *A61K 35/15* | (2015.01) | |
| *A61K 39/00* | (2006.01) | |
| *A61K 9/51* | (2006.01) | |

(52) U.S. Cl.
CPC .............. *A61K 38/06* (2013.01); *A61K 35/15* (2013.01); *A61K 39/0225* (2013.01); *A61K 39/39* (2013.01); *A61K 9/5153* (2013.01); *A61K 2039/6006* (2013.01); *Y02A 50/401* (2018.01); *Y02A 50/478* (2018.01); *Y02A 50/48* (2018.01)

(58) Field of Classification Search
None
See application file for complete search history.

(56) References Cited

U.S. PATENT DOCUMENTS

| 9,925,230 | B2 | 3/2018 | Budd |
| 2016/0030538 | A1 | 2/2016 | Budd |

OTHER PUBLICATIONS

Kim et al (PLoS One. May 2008. 3(5): 1-12).*
Blagosklonny, MV (Leukemia. 2001. 15:936-941).*
Hensley et al (Biol Chem. Jul. 1, 2013; 394(7): 831-843).*
Stupack, D. (Cancer Lett. May 2013. 333(2): 133-140).*
Balbi et al., Increased numbers of T lymphocytes with gamma delta-positive antigen receptors in a subgroup of individuals with pulmonary sarcoidosis. J Clin Invest. May 1990;85(5):1353-61.
Boatright et al., Activation of caspases-8 and -10 by FLIP(L). Biochem J. Sep. 1, 2004;382(Pt 2):651-7.
Born et al., Immunoregulatory functions of gamma delta T cells. Adv Immunol. 1999;71:77-144. Review.
Brennan et al., T cells expressing gamma delta chain receptors in rheumatoid arthritis. J Autoimmun. Aug. 1988;1(4):319-26.
Collins et al., Activation of gamma delta T cells by Borrelia burgdorferi is indirect via a TLR-and caspase-dependent pathway. J Immunol. Aug. 15, 2008;181(4):2392-8.
Collins et al., Lyme arthritis synovial gammadelta T cells instruct dendritic cells via fas ligand. J Immunol. Nov. 1, 2005;175(9):5656-65.
Cruz et al., Phagocytosis of Borrelia burgdorferi, the Lyme disease spirochete, potentiates innate immune activation and induces apoptosis in human monocytes. Infect Immun. Jan. 2008;76(1):56-70. Epub Oct. 15, 2007.
Dohrman et al., Cellular FLIP long form augments caspase activity and death of T cells through heterodimerization with and activation of caspase-8. J Immunol. Jul. 1, 2005;175(1):311-8.
Everts et al., TLR-driven early glycolytic reprogramming via the kinases TBK1-IKKε supports the anabolic demands of dendritic cell activation. Nat Immunol. Apr. 2014;15(4):323-32. doi: 10.1038/ni.2833. Epub Feb. 23, 2014.
Feoktistova et al., cIAPs block Ripoptosome formation, a RIP1/caspase-8 containing intracellular cell death complex differentially regulated by cFLIP isoforms. Mol Cell. Aug. 5, 2011;43(3):449-63. doi:10.1016/j.molcel.2011.06.011. Epub Jul. 7, 2011.
Gordon et al., Alternative activation of macrophages: mechanism and functions. Immunity. May 28, 2010;32(5):593-604. doi:10.1016/j.immuni.2010.05.007. Review.
Helfer et al., Caspase-8 promotes cell motility and calpain activity under nonapoptotic conditions. Cancer Res. Apr. 15, 2006;66(8):4273-8.
Irmler et al., Inhibition of death receptor signals by cellular FLIP. Nature. Jul. 10, 1997;388(6638):190-5.
Kaiser et al., RIP3 mediates the embryonic lethality of caspase-8-deficient mice. Nature. Mar. 17, 2011;471(7338):368-72. doi:10.1038/nature09857. Epub Mar. 2, 2011.
Kalyan et al., Defining the nature of human γδ T cells: a biographical sketch of the highly empathetic. Cell Mol Immunol. Jan. 2013;10(1):21-9. doi:10.1038/cmi.2012.44. Epub Oct. 22, 2012. Review.
Kang et al., Caspase-8 serves both apoptotic and nonapoptotic roles. J Immunol. Sep. 1, 2004;173(5):2976-84.
Kennedy et al., Caspase activation is required for T cell proliferation. J Exp Med. Dec. 20, 1999;190(12):1891-6.
Koenig et al., The c-FLIPL cleavage product p43FLIP promotes activation of extracellular signal-regulated kinase (ERK), nuclear factor κb (NF-κb), and caspase-8 and T cell survival. J Biol Chem. Jan. 10, 2014;289(2):1183-91. doi: 10.1074/jbc.M113.506428. Epub Nov. 25, 2013.

(Continued)

*Primary Examiner* — Jennifer E Graser

(74) *Attorney, Agent, or Firm* — Wolf, Greenfield & Sacks, P.C.

(57) ABSTRACT

Methods and products for producing an antigen specific immune response are provided. The methods involve administration of a caspase inhibitor to a subject.

9 Claims, 8 Drawing Sheets

Specification includes a Sequence Listing.

(56) References Cited

OTHER PUBLICATIONS

Micheau et al., The long form of FLIP is an activator of caspase-8 at the Fas death-inducing signaling complex. J Biol Chem. Nov. 22, 2002;277(47):45162-71. Epub Sep. 4, 2002.

Misra et al., Caspase-8 and c-FLIPL associate in lipid rafts with NF-kappaB adaptors during T cell activation. J Biol Chem. Jul. 6, 2007;282(27):19365-74. Epub Apr. 26, 2007.

Oberst et al., Catalytic activity of the caspase-8-FLIP(L) complex inhibits RIPK3-dependent necrosis. Nature. Mar. 17, 2011;471(7338):363-7. doi:10.1038/nature09852. Epub Mar. 2, 2011.

Rust et al., Phenotypical and functional characterization of small intestinal TcR gamma delta + T cells in coeliac disease. Scand J Immunol. Apr. 1992;35(4):459-68.

Salmena et al., Essential role for caspase 8 in T-cell homeostasis and T-cell-mediated immunity. Genes Dev. Apr. 1, 2003;17(7):883-95. Epub Mar. 21, 2003.

Shi et al., Reduced immune response to Borrelia burgdorferi in the absence of γδ T cells. Infect Immun. Oct. 2011;79(10):3940-6. doi: 10.1128/IAI.00148-11. Epub Jul. 18, 2011.

Su et al., Requirement for caspase-8 in NF-kappaB activation by antigen receptor. Science. Mar. 4, 2005;307(5714):1465-8.

Tenev et al., The Ripoptosome, a signaling platform that assembles in response to genotoxic stress and loss of IAPs. Mol Cell. Aug. 5, 2011;43(3):432-48. doi: 10.1016/j.molcel.2011.06.006. Epub Jul. 7, 2011. Erratum in: Mol Cell. Aug. 19, 2011;43(4):689.

Thome et al., Viral FLICE-inhibitory proteins (FLIPs) prevent apoptosis induced by death receptors. Nature. Apr. 3, 1997;386(6624):517-21.

Vantourout et al., Six-of-the-best: unique contributions of γδ T cells to immunology. Nat Rev Immunol. Feb. 2013;13(2):88-100. doi: 10.1038/nri3384. Review.

Varfolomeev et al., Targeted disruption of the mouse Caspase 8 gene ablates cell death induction by the TNF receptors, Fas/Apo1, and DR3 and is lethal prenatally. Immunity. Aug. 1998;9(2):267-76.

Vincent et al., Apoptosis of Fas(high) CD4+ synovial T cells by borrelia-reactive Fas-ligand(high) gamma delta T cells in Lyme arthritis. J Exp Med. Dec. 1, 1996;184(6):2109-17.

Vincent et al., Lyme arthritis synovial gamma delta T cells respond to Borrelia burgdorferi lipoproteins and lipidated hexapeptides. J Immunol. Nov. 15, 1998;161(10):5762-71.

Yatim et al., Dying cells actively regulate adaptive immune responses. Nat Rev Immunol. Apr. 2017;17(4):262-275. doi: 10.1038/nri.2017. 9. Epub Mar. 13, 2017.

Yeh et al., Requirement for Casper (c-FLIP) in regulation of death receptor-induced apoptosis and embryonic development. Immunity. Jun. 2000;12(6):633-42.

\* cited by examiner

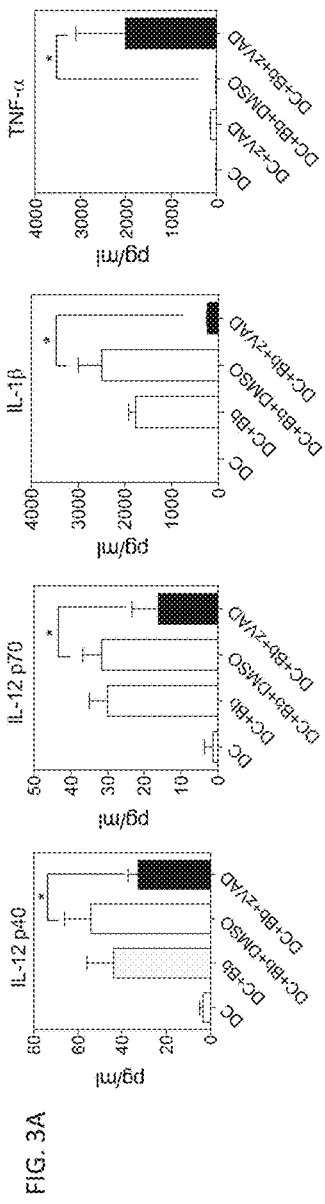
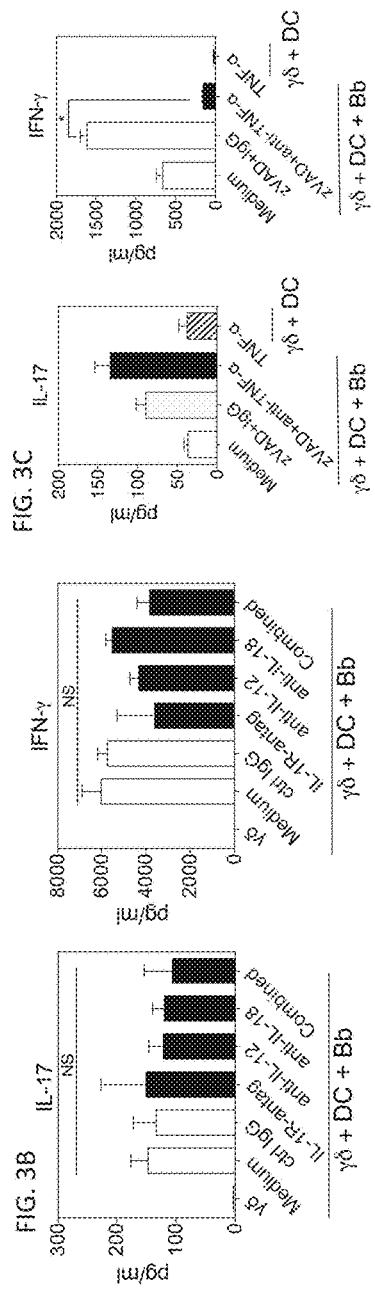
FIG. 3A
FIG. 3B
FIG. 3C
FIG. 3D

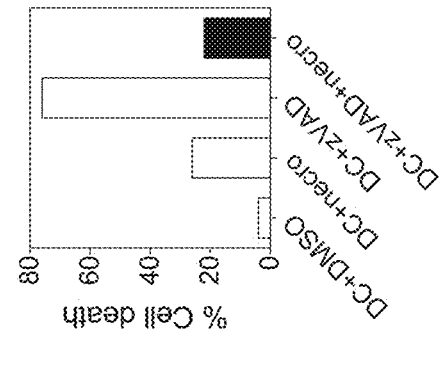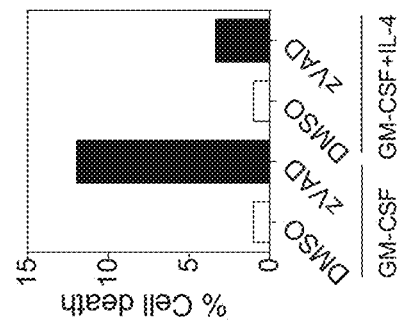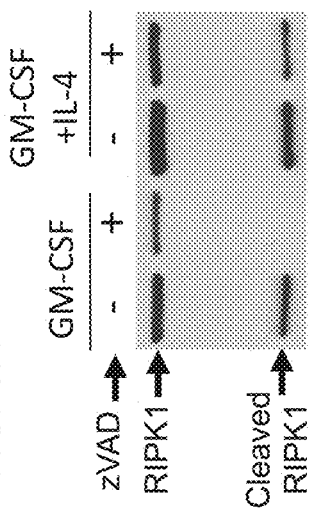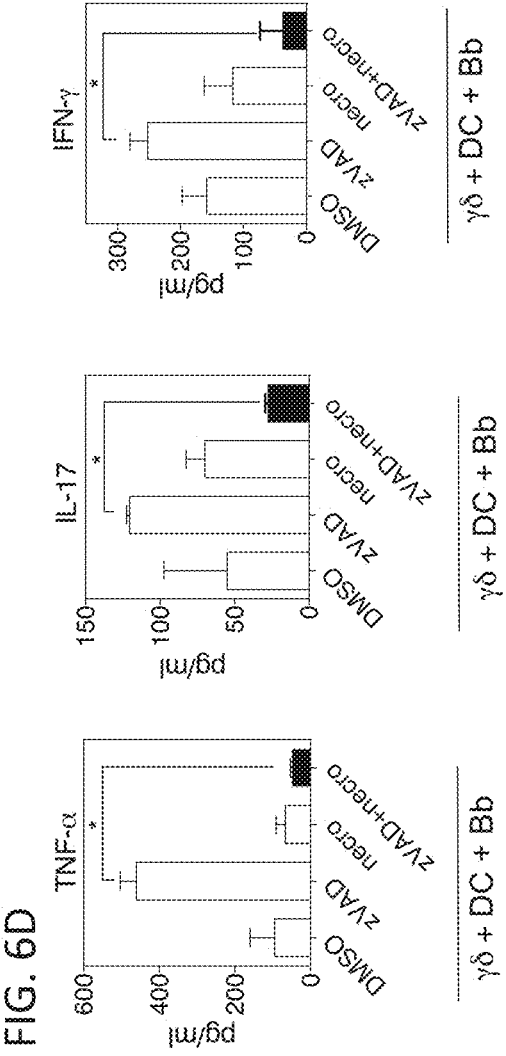

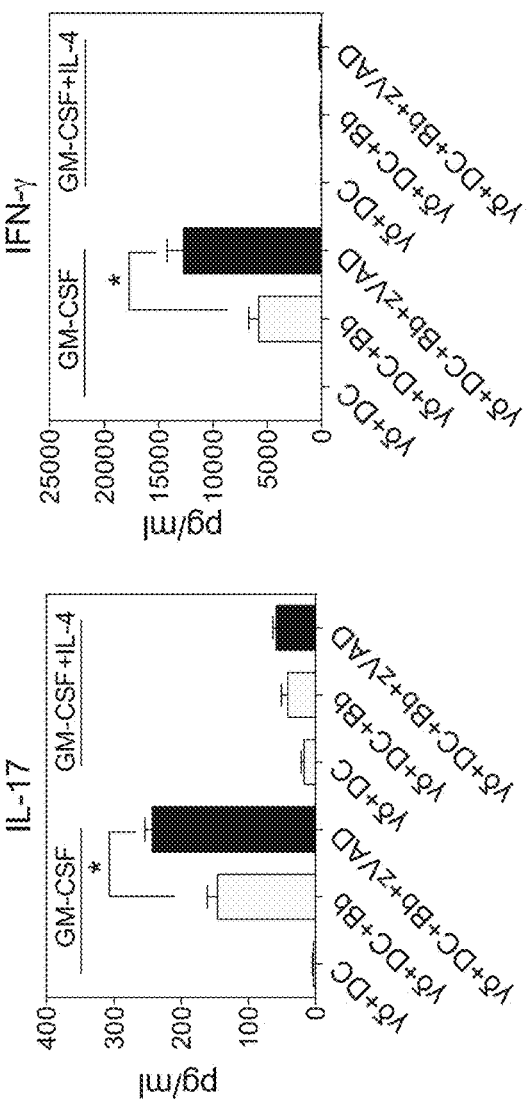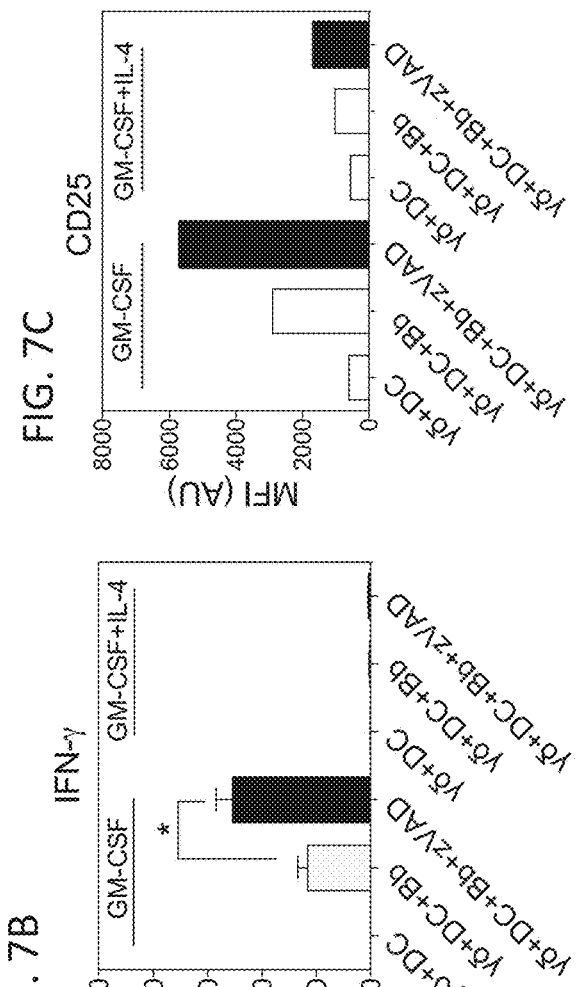

US 10,456,441 B2

AUGMENTING THE IMMUNE RESPONSE BY PROMOTING CELL DEATH OF IMMUNE CELLS

RELATED APPLICATIONS

This application is a divisional application which claims the benefit under 35 U.S.C. § 120 of U.S. application Ser. No. 14/806,047, entitled "AUGMENTING THE IMMUNE RESPONSE BY PROMOTING CELL DEATH OF IMMUNE CELLS", filed on Jul. 22, 2015, which claims priority under 35 U.S.C. § 119(e) to U.S. Provisional Application Ser. No. 62/027,641, entitled "AUGMENTING THE IMMUNE RESPONSE BY PROMOTING CELL DEATH OF IMMUNE CELLS," filed on Jul. 22, 2014, which are herein incorporated by reference in their entirety.

FEDERALLY SPONSORED RESEARCH

This invention was made with government support under R01 Grant AR43520, awarded by the National Institutes of Health. Accordingly, the government has certain rights in the invention.

BACKGROUND OF THE INVENTION

γδ T cells function at the interface between the innate and adaptive immune systems and have well-demonstrated roles in response to infection, autoimmunity, and tumors. A common characteristic of these seemingly disparate conditions may be cellular stress. Very few verified ligands for γδ T cells have been identified and these have been largely intact self-proteins with no obvious common structure. In addition, no traditional MHC-restricted recognition of ligands has been demonstrated for γδ T cells. Thus, the conditions under which ligands for γδ T cells are induced or exposed remain largely undefined.

SUMMARY OF THE INVENTION

It has been discovered according to aspects of the invention that γδ T cells function in the immune surveillance of cell stress, at least partly through the induction of necroptosis in bone marrow dendritic cells (BMDC) which upregulates or exposes expression of γδ T cell ligands. *Borrelia burgdorferi* stimulates both human and murine γδ T cells indirectly primarily via TLR2 signaling of dendritic cells. Presently, it has been observed that the induction of cell death of BMDC by inhibition of caspase activity paradoxically augments their ability to activate γδ T cells in response to *Borrelia* (data presented in Examples). This occurred via activation of the Ripoptosome and induction of necroptosis. Furthermore, upregulation of the stabilizer of caspase-8 activity, c-FLIP, by IL-4 not only greatly reduced the susceptibility of BMDC to cell death by caspase inhibition, but also considerably decreased their ability to activate γδ T cells.

The invention in aspects is a method of isolating a dendritic cell sample from a subject and contacting the dendritic cell sample with a caspase inhibitor to produce a modified dendritic cell sample.

The invention in other aspects is a method involving isolating a dendritic cell sample from a subject and contacting the dendritic cell sample with a caspase inhibitor to produce a modified dendritic cell sample. In some embodiments the method further involves administering the modified dendritic cell sample to a subject. In another embodiment the dendritic cell sample is a purified dendritic cell sample, wherein greater than 95% of the cells are dendritic cells. In some embodiments the dendritic cell sample is a mixture of dendritic cells and T cells. In some embodiments the method comprises contacting the dendritic cell with an antigen. In some embodiments, the method further comprises contacting the dendritic cell with an adjuvant. In another embodiment, the subject receiving the dendritic cells is a different subject than the subject from which the dendritic cells have been isolated. In some embodiments, the caspase inhibitor is a caspase 8 inhibitor. In other embodiments, the caspase inhibitor is a pan caspase inhibitor. In another embodiment, the pan caspase inhibitor is zVAD. In some embodiments, the caspase inhibitor is an anti-caspase antibody. In another embodiment, the caspase inhibitor is an inhibitory nucleic acid. In some embodiments, the caspase inhibitor is formulated in a nanoparticle.

In other aspects the invention is a method to promote an antigen-specific immune response in a subject by administering to the subject a caspase inhibitor in an effective amount to promote an antigen specific immune response. In some embodiments, an antigen is administered to the subject. In another embodiment, an adjuvant is administered to the subject. In some embodiments, the antigen is an infectious disease antigen. In other embodiments, the caspase inhibitor is a caspase 8 inhibitor. In some embodiments, the caspase inhibitor is a pan caspase inhibitor. In other embodiments, the pan caspase inhibitor is zVAD. In some embodiments, the caspase inhibitor is an anti-caspase antibody. In another embodiment, the caspase inhibitor is an inhibitory nucleic acid. In other embodiments, the caspase inhibitor is formulated in a nanoparticle.

The invention in aspects, is a method for vaccinating a subject against an infectious disease agent by administering a caspase inhibitor to the subject in an effective amount to induce an immune response against the infectious disease agent. In some embodiments, an infectious disease antigen is administered to the subject. In another embodiment, the subject has an infection. In other embodiments, the subject is at risk of exposure to an infectious disease agent. In another embodiment, the infectious disease agent is selected from the group consisting of *Borrelia burgdorferi, Escherichia coli, Acinetobacter baumannii, Helicobacter pyloris, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species.), *Streptococcus pneumoniae*, pathogenic *Campylobacter* sp *Enterococcus* sp., *Haemophilus influenzae, Bacillus antracis, Corynebacterium diphtherias, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira, Rickettsia,* and *Actinomyces israelii*. In some embodiments, an adjuvant is administered to the subject. In other embodiments, the caspase inhibitor is a caspase 8 inhibitor. In some embodiments, the caspase inhibitor is a pan caspase inhibitor. In another embodiment, the pan caspase inhibitor is zVAD. In another embodiment, the caspase inhibitor is an anti-caspase antibody. In some embodiments, the caspase inhibitor is an inhibitory nucleic acid. In other embodiments, the caspase inhibitor is formulated in a nanoparticle.

In other aspects the invention is a method for treating cancer in a subject, by administering to a subject having cancer a caspase inhibitor in an effective amount to treat the cancer. In some embodiments, a cancer antigen is administered to the subject. In another embodiment, the subject has a cancer selected from the group consisting of lymphoma, leukemia, fibrosarcoma, myxosarcoma, liposarcoma, chondrosarcoma, osteogenic sarcoma, chordoma, angiosarcoma, endotheliosarcoma, lymphangiosarconia, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinorna, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, lung cancer, bladder carcinoma, epithelial carcinoma, glioma, astrocytoma, meduilobias oma, craniopharyngioma, ependymoma, pinealoma, hemangiohlastoma, acoustic neuroma, oligodendroglioma, meningioma, melanoma, neuroblastoma, and retinoblastoma. In other embodiments, an adjuvant is administered to the subject. In some embodiments, the caspase inhibitor is a caspase 8 inhibitor. In another embodiment, the caspase inhibitor is a pan caspase inhibitor. In other embodiments, the pan caspase inhibitor is zVAD. In some embodiments, the caspase inhibitor is an anti-caspase antibody. In another embodiment, the caspase inhibitor is an inhibitory nucleic acid. In some embodiments, the caspase inhibitor is formulated in a nanoparticle.

In yet another aspect, the invention is a method for promoting dendritic cell survival, by contacting a dendritic cell with a survival promoting caspase inhibitor in an effective amount to enhance survival of the dendritic cell.

In other aspects, the invention is a composition comprising a caspase inhibitor, an antigen, and a carrier. In some embodiments, the composition is a vaccine. In other embodiments, the carrier is a nanoparticle. In another embodiment, the nanoparticle is a polymeric nanoparticle. In some embodiments, the caspase inhibitor is a caspase 8 inhibitor. In other embodiments, the caspase inhibitor is a pan caspase inhibitor. In some embodiments, the pan caspase inhibitor is zVAD. In another embodiment, the caspase inhibitor is an anti-caspase antibody. In some embodiments, the caspase inhibitor is an inhibitory nucleic acid. In other embodiments, the composition further comprises an adjuvant. In some embodiments, the antigen is an infectious disease antigen. In another embodiment, the antigen is a cancer antigen.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A consists of two graphs showing the percentage of cell death resulting when BMDC cultivated using GM-CSF were given the indicated concentrations of the pan-caspase inhibitor, zVAD, or vehicle control DMSO. γδ T cells were also given zVAD at 50 μM. After 20 hours, cells were evaluated for cell death by TUNEL assay. FIG. 1B shows the production of IL-17 and IFN-γ, and the expression of CD25 in supernatants from γδ T cells and BMDC cultured separately or together in a 1:1 ratio in the absence or presence of B. burgdorferi sonicate (Bb) (10 μg/ml). Control DMSO or zVAD (50 μM) was added to some cultures. After 20 hours, supernatants were assessed for production of the γδ T cell cytokines IL-17 and IFN-γ by Bio-Plex, and CD25 expression by the γδ T cells using flow cytometry. FIG. 1C demonstrates that zVAD-treated BMDC can partially activate γδ T cells in the absence of Borrelia. Cell cultures were prepared as described in FIG. 1B except in the absence of B. burgdorferi. The asterisk (*) indicates $p<0.05$ by Student t-test.

FIGS. 3A-3D demonstrate that augmented activation of γδ T cells by caspase-inhibited BMDC involves a soluble factor. In FIG. 3A, BMDC were cultured without or with B. burgdorferi in the absence or presence of zVAD. After 20 h supernatants were assayed by Bio-Plex for the BMDC cytokines IL-12 p40, IL-12 p'70, IL-1β, and TNF-α. FIG. 3B shows γδ T cells and BMDC co-cultured with B. burgdorferi (γδ+DC+Bb) in the presence of medium alone, control IgG, IL-1Receptor antagonist (Anakinra, 200 ng/ml), anti-IL-12 (10 μg/ml), anti-IL-18 (10 μg/ml), or all three blockers (Combined). After 20 h, supernatants were collected and assayed for the γδ T cell cytokines IL-17 and IFN-γ. FIG. 3C shows γδ T cells and DC cultured with B. burgdorferi (Bb) either in the presence of zVAD, plus control IgG or anti-TNF-α (both 10 μg/ml), or in the absence of B. burgdorferi but with exogenous TNF-α (2.5 μg/ml). After 20 h, supernatants were collected and assayed for IL-17 and IFN-γ. FIG. 3D shows wild-type γδ T cells cultured with DC from either wild-type or TNF-α$^{-/-}$ mice with B. burgdorferi. Supernatants were harvested after 20 h and assayed for TNF-α, IL-17, or IFN-γ (*$p<0.05$ by one-way ANOVA followed by Tukey's post-test). Data were consistent in three experiments for FIGS. 3A-3C, and two experiments for FIG. 3D.

FIG. 4A shows γδ T cells cultured with supernatants (SN) previously obtained from 20 h cultures of BMDC plus *B. burgdorferi* with either DMSO or zVAD (50 μM). After an additional 20 h the γδ T cell supernatants were assayed for IL-17 and IFN-γ. FIG. 4B shows transwell cultures established in which γδ T cells were cultured in the lower chamber and DC cultured *B. burgdorferi* in the upper chamber with in the absence or presence of zVAD. After 20 h supernatants were evaluated for IL-17 and IFN-γ (*$p<0.05$ by one-way ANOVA followed by Tukey's post-test). Data were consistent in three experiments.

FIGS. 6A-6D consist of data demonstrating that zVAD inhibits caspase-mediated RIPK1 cleavage and induces BMDC cell death with GM-CSF but not with IL-4. FIG. 6A depicts the cleavage of RIPK1 in BMDC that were cultured for 7 days in GM-CSF or GM-CSF+IL-4 in the absence (DMSO) or presence of zVAD. FIG. 6B illustrates cell death by TUNEL assay in cells that underwent the same treatment as described in FIG. 6A. FIG. 6C is a graph illustrating the cell death of GM-CSF-cultivated BMDC following culture in the absence (DMSO) or presence of the RIPK1-inhibitor, Necrostatin (50 μM) in the absence or presence of zVAD (50 μM). FIG. 6D contains graphs indicating the concentrations of TNF-α, IL-17, and IFN-γ in supernatants 20 hours after cultures containing γδ T cells, BMDC, and *B. burgdorferi*, were given either control DMSO, zVAD alone, or zVAD+ Necrostatin. Supernatants were assayed after 20 hours for the indicated cytokines. (*indicates $p<0.05$ by one-way ANOVA followed by Tukey's post-test). Data were similar in three experiments.

FIGS. 7A-7C demonstrate that IL-4 inhibits the ability of BMDC to activate γδ T cells. BMDC grown with either GM-CSF or GM-CSF+IL-4 were mixed at a 1:1 ratio with γδ T cells in the absence or presence of *B. burgdorferi* and zVAD. After 20 hours, the supernatants were analyzed. FIG. 7A shows the concentrations of IL-17 in the resulting samples by Bio-Plex analysis. FIG. 7B illustrates the samples' IFN-γ concentration by Bio-Plex analysis. FIG. 7C depicts the surface CD25 on the γδ T cells measured by flow cytometry (*$p<0.05$ by one-way ANOVA followed by Tukey's post-test). Findings were consistent in three experiments.

FIG. 8A shows Freshly isolated murine $CD4^+$ OT-II cells and BMDC cultured separately or together at a 1:1 ratio in the absence or presence of OVAp (1 μg/ml). After 20 h, supernatants were assessed for production of the IL-17 and IFN-γ. FIG. 8B shows human BMDC, cultured from peripheral blood monocytes with GM-CSF in the presence or absence of IL-4, were exposed to the indicated concentrations of zVAD for 20 h and then assessed for the percentage of dead cells. FIG. 8C shows human synovial Vδ1 clone Bb15 cultured with human DC cultured with GM-CSF alone or GM-CSF+IL-4 in a 1:1 ratio with *B. burgdorferi* (10 μg/ml), in the absence or presence of zVAD (50 μM). After 20 h supernatants were assessed for IFN-γ production. (*$p<0.05$ by one-way ANOVA followed by Tukey's post-test). Data are representative of two experiments.

DETAILED DESCRIPTION OF THE INVENTION

Figure 1A:
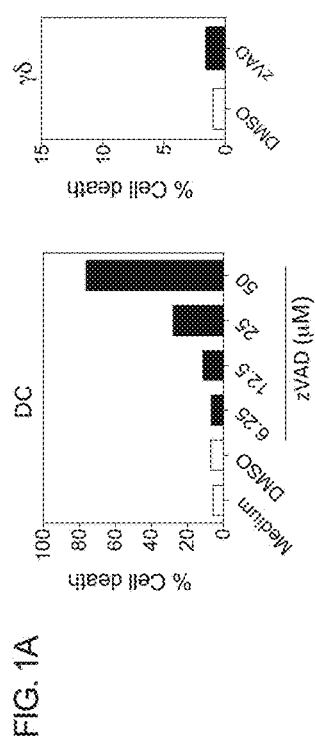
FIGS. 1A-1C indicate that the inhibition of caspase activity in BMDC results in cell death but an enhanced ability to stimulate γδ T cells.

γδ T cells represent a unique lymphoid lineage that functions at the interface between the innate and adaptive immune responses (1-3). Clues to their specificity and function derive in part from the observation that they frequently localize to selected areas, including epithelial barriers and sites of inflammation, such as synovial fluid in Lyme and rheumatoid arthritis (4-7). This is particularly striking in mice where a monoclonal γδ T cell subset expressing an invariant and canonical Vγ5/Vδ1 populates exclusively the epidermis, whereas another subset of Vγ6/Vδ1 T cells colonizes specifically the female reproductive tract, the tongue, and the lung (3). The limited diversity of actually expressed TCR-γδ, despite the potential for gene rearrangement of a large diversity of receptors, suggests a possibly limited repertoire of TCR-γδ ligands. In striking contrast to αβ T cells or B cells, which eliminate self-reactive cells during development, γδ T cells appear to be biased toward recognition of self-antigens (2). Furthermore, growing evidence suggests that many of these self-ligands may be induced under conditions of stress in a variety of cell types (2). As such γδ T cells may have evolved to respond to certain host-derived molecules during the early phases of infection, metabolic cell stress, or even cell death.

The response of γδ T cells to the Lyme disease spirochete, *Borrelia burgdorferi*, has been previously used as a model system to examine the activation of certain γδ T cells in mice and humans (5, 8-11). It has been determined that γδ T cells respond indirectly to *Borrelia* via TLR2 activation on antigen presenting cells, such as monocytes or dendritic cells (DC) (9). In response, the γδ T cells can then promote full activation of DC (10). Moreover, mice deficient for γδ T cells manifest a reduced adaptive immune response to *Borrelia* infection, greater bacterial burden, and enhanced cardiac inflammation (11). *Borrelia* can also promote cell death of macrophages in a TLR2-dependent manner (12). These collective findings raise the issue whether activation of γδ by *Borrelia* either requires or is enhanced in the presence of cell death.

It was discovered herein that bone marrow-derived dendritic cells (BMDC) derived with GM-CSF were exquisitely sensitive to caspase inhibition and rapidly underwent cell death. However, despite cell death, these BMDC manifested an enhanced ability to activate γδ T cells in the presence of infectious agents such as *Borrelia*. Both the BMDC death and enhanced activation of γδ T cells were reversed by Necrostatin, an inhibitor of RIPK1. Of particular interest was that addition of IL-4 during in vitro generation of BMDC strongly upregulated the expression of c-FLIP, promoting greater levels of caspase-8 activity, resistance to death by caspase inhibition, and yet paradoxically a considerably reduced ability to activate γδ T cells. The findings support the view that ligands for γδ T cells are induced or exposed in stressed or dying cells during the process of necroptosis.

The invention in some aspects is a method for promoting an antigen specific immune response in a subject. An antigen specific immune response is an immune response characterized by a T cell response (cellular immune response) and/or a B cell response (humoral immune response) that is directed at an antigen. For example, activated CD4 T cells can coordinate and orchestrate $CD8^+$ cytotoxic T cells and B cells in an antigen-specific response.

The subject is administered a caspase inhibitor in order to produce the antigen specific immune response. A caspase is a cysteine protease having strict specificity for cleaving peptide sequences C-terminal to aspartic acids residues. At least 14 caspase isozymes have been identified in humans with numerous reported activities. Caspases are often subcategorized as either pro-apoptotic or pro-inflammatory enzymes.

A wide variety of caspase inhibitors are commercially available and useful in the methods and products described herein. They include, for example, small molecule inhibitors such as IDN-1965, active-site mimetic peptide ketones such as zVAD-FMK, IDN-6556, Pralnacasan (VX-740), VX-765, Boc-D-fmk (tert-butyloxycarbonyl-Asp(O-methyl)-fluoromethyl ketone, z-VAD-fmk (N-benzyloxycarbonyl-Val-Ala-Asp-fluoromethyl ketone; and Q-VD-OPh (N-(2(quinolyl)valylaspartyl-(2,6-difluorophenoxy)methyl ketone.

Broad spectrum caspase inhibitors, such as the active-site mimetic peptide ketones (i.e. zVAD-FMK), have been highly effective in animal models in reducing cell death after ischemia in multiple tissues. Also nonselective caspase inhibitors have decreased apoptosis in animal models of amyotrophic lateral sclerosis, Parkinson's disease, and sepsis. Idun Pharmaceutical's IDN-6556, a broad spectrum caspase inhibitor, is showing promise in human trials for preserving liver function during hepatitis C virus infection without exhibiting serious side-effects, validating the use of caspase inhibitors in humans. The broad-range caspase inhibitor IDN-1965 has been employed in continuous infusion studies for blocking cardiac damage during heart failure in a murine model. To date, at least three caspase 1 inhibitors have entered clinical evaluation including Pralnacasan (VX-740), IDN-6556 and VX-765. All three agents are active site inhibitors that act through reversible (Pralnacasan and VX-765) or irreversible (IDN-6556) covalent modification of the catalytic cysteine residue. Boc-D-fmk and z-VAD-fmk are sold by Enzyme Systems Products, CalBiochem or R&D Systems. The Boc (tert-butyloxycarbonyl) and z (N-benzyloxycarbonyl) groups serve to block the amino acid sequences D (Asp) or VAD (Val-Ala-Asp), while the fluoromethyl ketone group in the carboxy-terminal position facilitates membrane permeability. Q-VD-OPh (N-(2(quinolyl)valylaspartyl-(2,6-difluorophenoxy)methyl ketone; Enzyme Systems Products, CalBiochem or R&D Systems), is another caspase inhibitor that may have increased efficacy, stability and permeability as compared with inhibitors having a carboxy-terminal group of the fluoromethyl ketone (fmk) type, and reduced toxicity.

In some preferred embodiments the caspase inhibitor is a caspase 8 inhibitor. Caspase-8 activity appears to be critical for the survival and proliferation of T lymphocytes as well as a variety of other cell types, and caspase-8-deficient mice are embryonic lethal. Specifically, caspase-8 is known to promote cell survival through the cleavage of Receptor Interacting Protein Kinase 1 (RIPK1). Cleaved RIPK1 acts as an inhibitor of the ability of full-length RIPK1 to form a complex known as the Ripoptosome, containing FADD, caspase-8, and RIPK1, which induces cell necroptosis. Caspase-8 activity in proliferating cells is maintained by the caspase-8 paralogue, c-FLIP, which lacks caspase enzymatic activity but contains instead a C-terminal loop that activates caspase-8 when these molecules heterodimerize.

The caspase inhibitor may also be a pan caspase inhibitor. A pan caspase inhibitor is a broad spectrum inhibitor that acts on more than one caspase. An example of a pan caspase inhibitor is zVAD.

Alternatively the caspase inhibitor may be an antibody or an inhibitory nucleic acid. Antibodies include anti-caspase antibodies as well as anti-cFLIP antibodies. An anti-caspase antibody is an antibody which binds specifically with a caspase and interferes with caspase activity. Anti-caspase antibodies are commercially available from companies such as Abcam, Lifetechnologies, Sigma Aldrich, EMD Millipore, Genetex, Enzo Lifesciences, Fitzgerald Industries, and Pierce Antibodies.

An anti-c-FLIP antibody is an antibody which binds specifically with c-FLIP and interferes with c-FLIP binding to or activation of caspase. Anti-c-FLIP antibodies are commercially available from companies such as Abcam, EMD Millipore, Genetex, Enzo Lifesciences, Cell Signaling Technology, Santa Cruz Biotechnology, and BioVision Inc.

The caspase inhibitor may be an siRNA to a caspase or c-FLIP. For example, the caspase inhibitor may be an siRNA to an caspase selected from the group consisting of caspase-1, caspase-2, caspase-3, caspase-4, caspase-5, caspase-6, caspase-7, caspase-8, caspase-9, caspase-10, caspase-11, caspase-12, and caspase-13. In a preferred embodiment, the caspase inhibitor is an siRNA to caspase-8 or c-FLIP. In other embodiments, the caspase inhibitor is a combination of siRNAs to a combination of caspases and/or c-FLIP. siRNAs are commercially available and can also be custom ordered from Dharmacon. The nucleotide sequences of caspases and/or c-FLIP molecules are well known in the art and can be used by one of skill in the art using art recognized techniques in combination with the guidance set forth herein to produce the appropriate siRNA molecules. Amino acid sequences for human caspase 8 can be found for instance in UniProtKB reference number Q14790 (CASP8 HUMAN). An exemplary sequence for isoform 1 is: MDFSRNLYDI GEQLDSEDLA SLKFLSLDYI PQRKQEPIKD ALMLFQRLQE KRMLEESNLS FLKELLFRIN RLDLLITYLN TRKEEMEREL QTPGRAQISA YRVMLYQISE EVSRSELRSF KFLLQEEISK CKLDDDMNLL DIFIEMEKRV ILGEGKLDIL KRVCAQINKS LLKIINDYEE FSKERSSSLE GSPDEFSNGE ELCGVMTISD SPREQDSESQ TLDKVYQMKS KPRGYCLIIN NHNFAKAREK VPKLHSIRDR NGTHLDAGAL TTTFEELHFE IKPHDDCTVE QIYEILKIYQ LMDHSNMDCF ICCILSHGDK GIIYGTDGQE APIYELTSQF TGLKCP SLAG KPKVFFIQAC QGDNYQKGIP VETDSEEQPY LEMDLSSPQT RYIPDEADFL LGMATVNNCV SYRNPAEGTW YIQSLCQSLR ERCPRGDDIL TILTEVNYEV SNKDDKKNMG KQMPQPTFTL RKKLVFPSD (SEQ ID NO: 1). siRNA can be designed from the nucleic acid sequences encoding this protein or from nucleic acid sequences provided in public databases such as genbank.

Small interfering nucleic acid (siNA) include, for example: microRNA (miRNA), small interfering RNA (siRNA), double-stranded RNA (dsRNA), and short hairpin RNA (shRNA) molecules. An siNA useful in the invention can be unmodified or chemically-modified. An siNA of the instant invention can be chemically synthesized, expressed from a vector or enzymatically synthesized. Such methods are well known in the art. In one embodiment, one of the strands of the double-stranded siNA molecule comprises a nucleotide sequence that is complementary to a nucleotide sequence of a target RNA or a portion thereof, and the second strand of the double-stranded siNA molecule comprises a nucleotide sequence identical to the nucleotide sequence or a portion thereof of the targeted RNA. In another embodiment, one of the strands of the double-stranded siNA molecule comprises a nucleotide sequence that is substantially complementary to a nucleotide sequence of a target RNA or a portion thereof, and the second strand of the double-stranded siNA molecule comprises a nucleotide sequence substantially similar to the nucleotide sequence or a portion thereof of the target RNA. In another embodiment, each strand of the siNA molecule comprises about 19 to about 23 nucleotides, and each strand comprises at least about 19 nucleotides that are complementary to the nucleotides of the other strand.

Other inhibitor molecules that can be used include ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins.

Caspase inhibitors are effective therapeutic agents for human vaccination, cancer immunotherapy, and general enhancement of immune function. The caspase inhibitors are useful in some aspects of the invention as a vaccine for the treatment of a subject at risk of developing an infection with an infectious organism or a cancer in which a specific cancer antigen has been identified or a subject having an infectious disease or cancer. When the caspase inhibitor is a vaccine, it is typically administered with an antigen and optionally with another adjuvant for prophylactic or therapeutic treatment.

The caspase inhibitors can also be given alone i.e., without concurrent administration of the antigen for protection against or treatment of infection or cancer if delivered in a manner that results in the production of an antigen specific immune response. For instance it is administered when the subject has an antigen in the body, when the antigen is administered to the subject in a separate vehicle concurrently with or at a different time than the caspase inhibitor, i.e. within 1, 2, 3, 4, 5, 6, 7, 8, 9, 10, 11, 12, 15, 20, 24, or 48 hours before or after administration of the caspase inhibitor. A subject at risk as used herein is a subject who has any risk of exposure to an infection causing pathogen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism has been identified. Subjects at risk of developing infection also include general populations to which a medical agency recommends vaccination with a particular infectious organism antigen.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a caspase inhibitor, the subject may be able to kill the cancer cells as they develop. If a tumor begins to form in the subject, the subject will develop a specific immune response against the tumor antigen.

In addition to the use of the caspase inhibitors for prophylactic treatment, the invention also encompasses the use of the caspase inhibitors for the treatment of a subject having an infection or a cancer.

A subject having an infection is a subject that has been exposed to an infectious pathogen and has acute or chronic detectable levels of the pathogen in the body. The caspase inhibitors can be used with or without an antigen to mount an antigen specific immune response that is capable of reducing the level of or eradicating the infectious pathogen. An infectious disease, as used herein, is a disease arising from the presence of a foreign microorganism in the body.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat cancer and tumors and infections in non-human subjects as well as human subjects. Cancer is one of the leading causes of death in companion animals (i.e., cats and dogs).

As used herein, the term treat, treated, or treating when used with respect to an disorder such as an infectious disease or cancer refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

In the instances when the caspase inhibitor is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the caspase inhibitor are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the caspase inhibitor. For instance, in a subject at risk of developing a cancer or an infectious disease, the subject may be administered the caspase inhibitor on a regular basis when that risk is greatest, i.e., after exposure to a cancer causing agent. Additionally the caspase inhibitor may be administered to travelers before they travel to foreign lands where they are at risk of exposure to infectious agents. Likewise the caspase inhibitor may be administered to soldiers or civilians at risk of exposure to biowarfare to induce an antigen specific immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites. The term antigen broadly includes any type of molecule which is recognized by a host immune system as being foreign. Antigens include but are not limited to cancer antigens and microbial antigens.

A cancer antigen as used herein is a compound, such as a peptide or protein, associated with a tumor or cancer cell surface and which is capable of provoking an immune response when expressed on the surface of an antigen presenting cell in the context of an MEW molecule. Cancer antigens can be prepared from cancer cells either by preparing crude extracts of cancer cells, for example, as described in Cohen, et al., 1994, Cancer Research, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of infectious viruses that have been found in humans and are useful for formulating in whole or in part as a microbial antigen include but are not limited to: Retroviridae (e.g. human immunodeficiency viruses, such as HIV-1; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis, hepatitis C; Norwalk and related viruses, and astroviruses).

Gram positive bacteria serving as antigens in vertebrate animals include, but are not limited to, Pasteurella species, Staphylococci species and Streptococcus species. Gram negative bacteria include, but are not limited to, *Escherichia coli, Pseudomonas* species, and *Salmonella* species. Specific examples of infectious bacteria include but are not limited to: *Helicobacter pyloris, Borelia burgdorferi, Legionella pneumophilia, Mycobacteria* sps. (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia, Actinomyces israelii* and *Chlamydia.*

Examples of infectious fungi include: *Cryptococcus neoformans, Histoplasma capsulatum, Coccidioides immitis, Blastomyces dermatitidis, Chlamydia trachomatis* and *Candida albicans*. Other infectious organisms (i.e., protists) include: *Plasmodium* such as *Plasmodium falciparum, Plasmodium malariae, Plasmodium ovale, Plasmodium vivax, Toxoplasma gondii* and *Shistosoma.*

Other medically relevant microorganisms have been descried extensively in the literature, e.g., see C. G. A. Thomas, "Medical Microbiology", Bailliere Tindall, Great Britain 1983, the entire contents of which is hereby incorporated by reference.

Sub-unit vaccines containing anti-microbial antigens and which can be employed as a component of the vaccines are typically recombinant protein-based antigens. Examples of such anti-microbial recombinant protein-based antigens include *Borrelia burgdorferi* antigens, Hepatitis B protective antigens, Herpes Simplex Virus antigens, Influenza antigens, Congenital cytomegalovirus (CMV) antigens, Tuberculosis antigens, HIV antigens, Diphtheria antigens, Tetanus antigens, Pertussis antigens and Yersinia pestis protective antigens, such as antigens comprising one, two or more antigenic proteins, or an anthrax protective antigen, such as recombinant protective antigen (rPA).

The term substantially purified as used herein refers to a molecule such as a polypeptide, carbohydrate, nucleic acid etc. which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens such as polysaccharides, small molecule, mimics etc. are included within the invention.

The caspase inhibitors of the invention may optionally be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and trypars-amide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir;

Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

Caspase inhibitors can be combined with other therapeutic agents such as adjuvants to enhance immune responses. The caspase inhibitor and other therapeutic agent may be administered simultaneously or sequentially. When the other therapeutic agents are administered simultaneously they can be administered in the same or separate formulations, but are administered at the same time. The other therapeutic agents are administered sequentially with one another and with caspase inhibitor, when the administration of the other therapeutic agents and the caspase inhibitor is temporally separated. The separation in time between the administration of these compounds may be a matter of minutes or it may be longer. Other therapeutic agents include but are not limited to adjuvants, cytokines, antibodies, antigens, etc.

An adjuvant is any molecule or compound which can stimulate the humoral and/or cellular immune response. Adjuvants include, for instance, adjuvants that create a depo effect, immune stimulating adjuvants, and adjuvants that create a depo effect and stimulate the immune system.

The caspase inhibitors may also be administered in conjunction with an anti-cancer therapy. Anti-cancer therapies include cancer medicaments, radiation and surgical procedures. As used herein, a "cancer medicament" refers to a agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

In one embodiment, the cancer medicament is a chemotherapeutic agent selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate. In an important embodiment, the cancer medicament is taxol.

In another embodiment, the cancer medicament is an immunotherapeutic agent selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

Additionally, the methods of the invention are intended to embrace the use of more than one cancer medicament along with the caspase inhibitors. As an example, where appropriate, the caspase inhibitors may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The term effective amount of a caspase inhibitor refers to the amount necessary or sufficient to realize a desired biologic effect. For example, an effective amount of a caspase inhibitor administered with an antigen for inducing an antigen specific immune response is that amount necessary to cause the development of specific antibodies in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular caspase inhibitor being administered the size of the subject, or the severity of the disease or condition. One of ordinary skill in the art can empirically determine the effective amount of a particular caspase inhibitor and/or antigen and/or other therapeutic agent without necessitating undue experimentation.

Subject doses of the compounds described herein typically range from about 0.1 µg to 10 mg per administration, which depending on the application could be given daily, weekly, or monthly and any other amount of time there between. More typically doses range from about 10 µg to 5 mg per administration, and most typically from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for caspase inhibitors and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the caspase inhibitor can be administered to a subject by any mode that delivers the caspase inhibitor to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (i.e., caspase inhibitors, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the caspase inhibitor or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the caspase inhibitor may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the caspase inhibitor either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the caspase inhibitors. The caspase inhibitor is delivered to the lungs of a mammal while inhaling and traverses across the lung epithelial lining to the blood stream.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of caspase inhibitor. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified caspase inhibitor may also be prepared in different formulations depending on the type of chemical modification or the type of device employed.

Formulations suitable for use with a nebulizer, either jet or ultrasonic, will typically comprise caspase inhibitor dissolved in water at a concentration of about 0.1 to 25 mg of biologically active caspase inhibitor per mL of solution. The formulation may also include a buffer and a simple sugar (e.g., for caspase inhibitor stabilization and regulation of osmotic pressure). The nebulizer formulation may also contain a surfactant, to reduce or prevent surface induced aggregation of the caspase inhibitor caused by atomization of the solution in forming the aerosol.

Formulations for use with a metered-dose inhaler device will generally comprise a finely divided powder containing the caspase inhibitor suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing caspase inhibitor and may also include a bulking agent, such as lactose, sorbitol, sucrose, or mannitol in amounts which facilitate dispersal of the powder from the device, e.g., 50 to 90% by weight of the formulation. The caspase inhibitor should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The caspase inhibitors and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a caspase inhibitor and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The vaccines and compositions of the invention may be formulated in a nanoparticle or microparticle. Nanoparticles and microparticles are small discrete particles that may be loaded with, coated with or encapsulate active agents. The nanoparticles and microparticles may be substantially spherical or oblong in shape or may be a mix of different shapes. The term "substantially spherical," as used herein, means that the shape of the particles does not deviate from a sphere by more than about 10%. The nanoparticle or microparticle may be solid or hollow or partially solid or hollow.

Nanoparticles typically have a size range in the nanometer scale, i.e., from about 1 nm to about 999 nm or alternatively, from about 1 nm to about 100 nm. The size in some aspects refers to the average or median diameter of a plurality of nanoparticles when a plurality of nanoparticles are intended. Microparticles have a size of 1 micron or greater.

Nanoparticles and microparticles may be polymeric particles. Polymeric particles and methods of making polymeric particles are well known in the art. In some embodiments, the particle is comprised of one or more biocompatible materials, e.g., biocompatible polymers, carbohydrates, or proteins, e.g., selected from the group consisting of poly(lactic-co-glycolic acid (PLGA), polyglutamic acid (PG), dextran, hyaluronic acid, poly(citrate), poly(glycerol sebacate), elastin, chitosan, poly(carbonate), poly(hydroxy acids), polyanhydrides, polyorthoesters, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly(valeric acid), and poly(lactide-co-caprolactone), ethylene vinyl acetate, copolymers and blends thereof. In certain embodiments, the biocompatible material is selected from the group consisting of poly(lactic-co-glycolic acid (PLGA), polyglutamic acid (PG) dextran, hyaluronic acid, poly(citrate), poly(glycerol sebacate), and poly(carbonate). Alternatively the particles may be formed by metals or metal oxides, such as Au, Fe, Ti.

The methods of the invention may be performed in vitro, ex vivo, or in vivo. The method in some aspects is a method for immunotherapy performed on dendritic cells ex vivo. When these methods are performed ex vivo they are performed by administering a modified dendritic cell sample that has been exposed to a caspase inhibitor outside of the body to a subject in need thereof.

An "ex vivo" method as used herein is a method which involves isolation of a dendritic cell sample from a subject, manipulation of the cell sample outside of the body, and reimplantation of the manipulated cell sample into a subject. The ex vivo procedure may be used on autologous or heterologous cells, but is preferably used on autologous cells. In preferred embodiments, the dendritic cell sample is isolated from peripheral blood or bone marrow, but may be isolated from any source of dendritic cells. When the ex vivo procedure is performed to specifically produce a modified dendritic cell sample active against a specific antigen, the dendritic cell sample may also be exposed to the antigen in addition to the caspase inhibitor. When returned to the subject, the modified dendritic cell sample activates T cells in vivo which are specific for the antigen. Ex vivo manipulation of dendritic cells for the purposes of cancer immunotherapy have been described in several references in the art, including Engleman, E. G., 1997, Cytotechnology, 25:1; Van Schooten, W., et al., 1997, Molecular Medicine Today, June, 255; Steinman, R. M., 1996, Experimental Hematology, 24, 849; and Gluckman, J. C., 1997, Cytokines, Cellular and Molecular Therapy, 3:187. The ex vivo manipulation of dendritic cells of the invention may be performed by routine ex vivo manipulation steps known in the art, but with the use of caspase inhibitor.

The dendritic cell sample may be a pure dendritic cell sample. i.e. 100% of the cells in the sample are dendritic cells or it may be a mixed population of cells. A mixed population of cells may be for instance a population wherein at least 50% of the cells in the sample are dendritic cells. Alternatively at least 60%, 70%, 80%, 90%, 95%, 96%, 97%, 98%, or 99% of the cells in the sample are dendritic cells.

The method may include the step of contacting the dendritic cell with an adjuvant and or an antigen prior to administering the cell to the subject.

The invention in another aspect is an isolated antigen-expressing dendritic cell population produced by the process of: exposing an isolated dendritic cell to a caspase inhibitor; optionally contacting the isolated dendritic cell with an antigen and/or adjuvant; and allowing the isolated dendritic cell to process and express the antigen. These cells are referred to herein as a modified dendritic cell sample.

EXEMPLIFICATION

In order that the invention described herein may be more fully understood, the following examples are set forth. The examples described in this application are offered to illustrate the compounds, pharmaceutical compositions, and methods provided herein and are not to be construed in any way as limiting their scope.

Example 1. Materials and Methods

Mice.

C57BL/6J mice were housed and bred in the AAALAC-approved animal facility at the University of Vermont (UVM), according to protocols approved by the UVM IACUC. Mice were used at 8 to 12 weeks of age for harvest of T cells from lymph nodes and spleens, and harvest of bone marrow cells. Original breeders were obtained from Jackson Laboratory (Bar Harbor, Me.).

Murine γδ T Cell Purification and Culture.

Spleens were isolated and disrupted through nylon mesh in RPMI 1640 with 25 mm Hepes (MediaTech, Herndon, Va.) containing 5% (v/v) bovine calf serum (HyClone, Logan, Utah). Erythrocyte lysis of splenocytes was performed using Geys solution. γδ T lymphocytes were enriched by negative selection using a magnetic bead system (Qiagen, Valencia, Calif.) in which splenocytes were incubated with a cocktail of rat monoclonal antibodies to mouse CD4 (clone GK 1.5), CD8 (clone Tib105), class II (clone M5/114/15/2), CD11b (clone M1/70), and B220 (CD45R) (clone RA3-6B2). Cells were washed three times and then rocked with goat anti-rat conjugated magnetic beads at a 10:1 ratio of beads to cell at 4° C. for 45 min. Magnetic depletion was used to remove bead-bound cells. Finally, enriched γδ T cells were resuspended in complete medium (RPMI 1640 (Mediatech, Inc., Herndon, Va., USA), 2.5 mg/ml glucose (Sigma, St. Louis, Mo.), 10 mg/ml folate (Invitrogen, Carlsbad, Calif.), 110 µg/ml pyruvate (Invitrogen), $5\times10^{-5}$ M 2-mercaptoethanol (Sigma), 292.3 µg/ml glutamine (Invitrogen), 100 units/ml penicillin-streptomycin (Invitrogen), and 5% bovine calf serum). Purified γδ T cells were initially activated at a density of $1\times10^6$ cells/ml by plate-bound anti-TCR-γδ (5 µg/ml, clone GL-3), and recombinant human IL-2 (50 units/ml, Cetus). After 2 days, cells were removed from anti-TCR-γδ stimulation, supplied with fresh medium plus IL-2, and returned to culture at a density of $0.3\times10^6$ cells/ml. Cells were counted daily and supplied with fresh media containing 50 units/ml IL-2. At the time of experiments, typically day 7, cultures were routinely over 95% γδ T cells by pan-anti-γδ antibody staining, and approximately 45% Vγ1$^+$, and negative for Vγ2, Vδ4, and Vδ6 by flow cytometry (not shown). In addition, in some experiments freshly isolated splenic γδ T cells were prepared using anti-γδ-coated magnetic beads (Miltenyi Biotec) and magnet purification.

OT-II αβT Cell Cultures.

C57BL/6 OT-II mice contain CD4$^+$ T cells that respond to ovalbumin peptide (OVAp) 323-339 in the context of I-A$^b$ (27). OT-II T cells were cultured with C57BL/6 DC at a 1:1 ratio in the presence of OVAp (10 µg/ml) with or without zVAD (50 µM). Supernatants were collected after 20 h and analyzed for production of IFN-γ and IL-17 by Bio-Plex.

Human Lyme Arthritis Synovial γδ T Cell Clones.

γδ T cell clones were derived from synovial fluid T cells stimulated with *B. burgdorferi* sonicate (10 µg/ml) and then cloned at limiting dilution as previously described (8). All clones are of the Vδ1 subset by antibody staining and DNA sequencing (8). Clones were restimulated every 10-14 days in the presence of irradiated peripheral blood lymphocytes ($3\times10^5$/well), human recombinant IL-2 (10 U/ml), and 10 µg/ml of *B. burgdorferi*.

Bone Marrow Dendritic Cells (BMDC).

The preparation of bone marrow-derived dendritic cells (BMDC) was done according to the method of Lutz et al. (26) using GM-CSF (10 µg/ml PeproTech, Rocky Hill N.J.) or GM-CSF plus IL-4 (10 µg/ml, PeproTech). Cells were used on day 7.

Human Dendritic Cells.

Human monocytes were obtained as CD14$^-$ cells by magnetic bead purification (Miltenyi Biotech, Auburn, Calif.) from peripheral blood of healthy volunteers. Myeloid DC were prepared by culture of monocytes in AIM V media plus 10% fetal calf serum (HyClone) with 800 U/ml of granulocyte-macrophage colony-stimulating factor (GM-CSF), (BioLegend, San Diego, Calif.) without or with 500 U/ml IL-4 (BioLegend).

Mixed Cultures.

Day 7 γδ T cells and BMDC were cultured either individually or together at a 1:1 ratio ($10^6$ cells/ml each). To some cultures the following reagents were added: a sonicate of *Borrelia burgdorferi* (10 µg/ml), zVAD-fmk (MP Biomedical, Santa Ana Calif.) at the doses indicated, necrostatin (50 µM, R&D Systems, Minneapolis, Minn.), anti-TNF-α (10 µg/ml, Calbiochem, Darnstadt, Germany), anti-TNF-α (10 µg/ml, Calbiochem, Darnstadt, Germany), anti-IL-1 Receptor antagonist, Anakinra (200 ng/ml, Amgen, Thousand Oaks, Calif.), anti-IL-12 (10 µg/ml, BioLegend San Diego, Calif.), anti-IL-18 (10 µg/ml, MBL, Woburn Mass.), or rat IgG (10 µg/ml Jackson Immunoresearch, West Grove Pa.). Transwell assays were performed using $1\times10^6$ γδ T cells in 1 ml of complete medium+IL-2 placed in the lower chamber, with $5\times10^5$ DC in 100 µl placed in the upper chamber. Supernatants were collected after 24 hours for cytokine analysis, and surface expression of CD25 by γδ T cells was determined by flow cytometry.

Cytokine/Chemokine Detection by the Multi-Plex Assay.

Cytokine levels of IFN-γ, IL-1β, IL-12p40, IL-12p70, IL-17, and TNF-α were detected using the Bio-Plex, Milli-Plex, or Luminex immunoassay (Bio-Rad; Millipore-EMD; R&D Systems, Minneapolis, Minn.) according to the manufacturer's protocol. Briefly, samples were run undiluted or diluted 1:10 in RPMI complete media. 50 µl of the magnetic bead working solution was added to each well, then 50 µl of appropriate samples or standards were then added to wells and incubated at room temperature for 30-120 min at 800 rpm on an IKA MS 3 digital shaker. After three washes with 100 µl Bio-Plex wash buffer, incubation with 25 µl of detection antibody solution was done at room temperature for 30-60 min on the shaker. Following another set of three washes, 50 µl of streptavidin-phycoerythrin (PE) in assay buffer was added to each well and incubated as described for the previous step. After an additional three washes, 125 µl of assay buffer was added. Sample data was analyzed with Bio-Plex Manager software.

Flow Cytometry.

The following monoclonal antibodies to murine cell surface molecules were purchased from BioLegend: PE-conjugated anti-CD25, APC-conjugated anti-TCR-γδ, and TNF-α neutralizing antibody. Rat IgG was purchased from Jackson Immunoresearch (West Grove, Pa.). For direct staining, single cell suspensions ($1\times10^6$ total cells per staining condition) were washed with cold (4° C.) PBS containing 1% (w/v) BSA fraction V (Sigma) (PBS/1% BSA), incubated with unconjugated rat IgG (50 µg/ml) for 15 min at 4° C., washed again, and then incubated with the appropriate antibodies in PBS/1% BSA. After washing, the cells were fixed with freshly made 1% (v/v) methanol-free formaldehyde (Ted Pella Inc., Redding, Calif.) in PBS/1% BSA.

Cell Death.

Cell death was examined by terminal deoxynucleotidyl transferase dUTP nick end labeling (TUNEL). Briefly, cells were stained for expression of cell surface molecules, and then fixed with 1% methanol-free formaldehyde followed by 70% ethanol. After washing, the TUNEL reaction was performed by incubating cells in 50 µl of reaction mix containing 10 units of terminal deoxribosyl transferase (TdT), 2.5 mM cobalt chloride in 1× TdT buffer, and 0.2 pmol/µl of FITC-dUTP (Roche, Indianapolis, Ind.) at 37° C. for 1 hour. The cells were washed twice and fixed in 1% methanol-free formaldehyde. Murine thymocytes were included as a positive control for apoptotic cells. Flow cytometry was performed on an LSRII (BD Biosciences, San Jose, Calif.) calibrated with compensation beads (BD Biosciences). Analysis was performed using FlowJo software (Tree Star, Inc., Ashland, Oreg.).

Detection of Active Caspases by Immunoblot.

Day 7 BMDC were lysed in Tris-buffer containing Complete Protease Inhibitor (Roche), 0.2% NP-40 (Roche), and biotin-VAD-fmk (10 µM, MP Biomedicals, Santa Ana, Calif.). Insoluble cell fragments were removed by centrifugation, and the protein concentration of the resulting whole cell lysates was determined by Bradford assay (BioRad, Hercules, Calif.). Whole cell lysates (30 µg per lane) were separated by SDS-PAGE. Precipitation of active caspases was performed by rocking 600 µg of whole cell lysates initially with sepharose 4B beads (Sigma) at 4° C. for 2 hours to remove nonspecific binding of proteins to the beads, followed by overnight rocking incubation with streptavidin-conjugated sepharose beads (Invitrogen) at 4° C. Release of biotin-VAD-fmk-labeled caspases from the streptavidin beads was achieved by heating to 95° C. for 10 min in Laemmli buffer. After gel electrophoresis, proteins were transferred to PVDF membranes (0.2 µm pore size, Bio-Rad), and immunoblots were performed using antibodies (1 µg/ml) against caspase-3, caspase-8 (both Cell Signaling, Danvers, Mass.), caspase-9 (Stressgen, Farmingdale, N.Y.), and RIPK1 (BD Biosciences).

Cytokine/Chemokine Detection by the Bio-Plex Assay.

Cytokine levels were detected using the MilliPlex or Bio-Plex immunoassay (Millipore-EMD; Bio-Rad) according to the manufacturer's protocol. Briefly, samples were run undiluted or diluted 1:10 in RPMI complete media. 50 µl of the magnetic bead working solution was added to each well, then 50 µl of appropriate samples or standards were added to wells and incubated at room temperature for 30 minutes at 300 rpm on an IKA MS 3 digital shaker. After three washes with 100 µl Bio-Plex wash buffer, samples were incubated with 25 µl of detection antibody solution was done at room temperature for 30 minutes on the shaker. Following another set of three washes, 50 µl of streptavidin-phycoerythrin (PE) in assay buffer was added to each well and incubated as described for the previous step. After an additional three washes, 125 µl of Bio-Plex assay buffer was added. Sample data was analyzed with Bio-Plex Manager software.

Statistical Analyses.

One-way ANOVA followed by Tukey's post test was conducted to assess differences among the various conditions in production of the indicated cytokines.

Figure 1B:
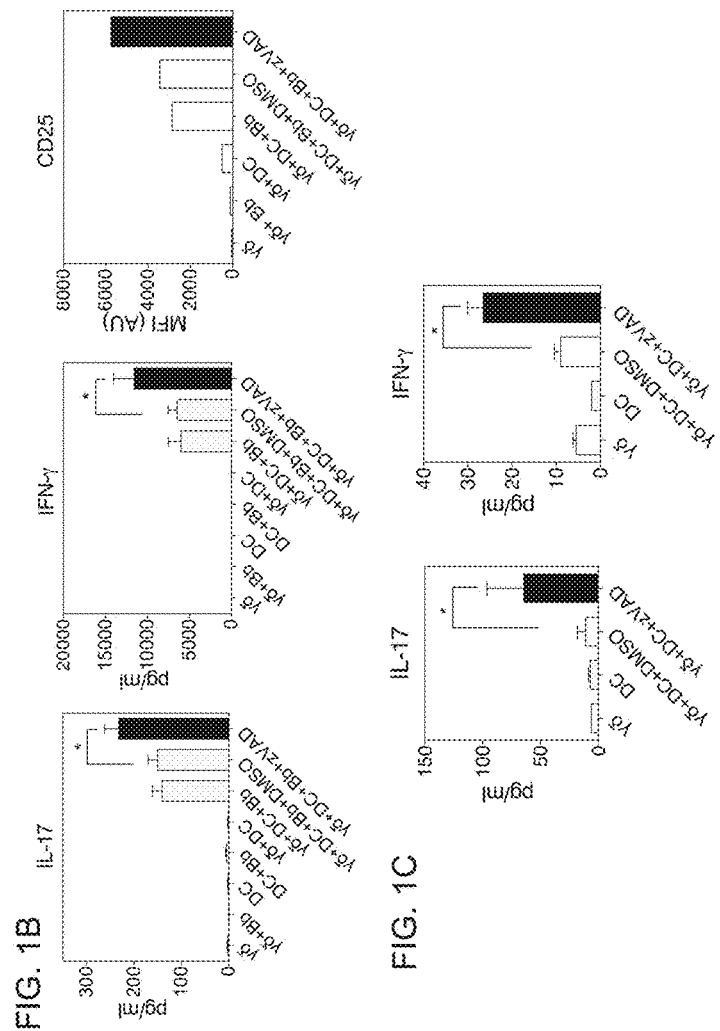
Figure 1C:
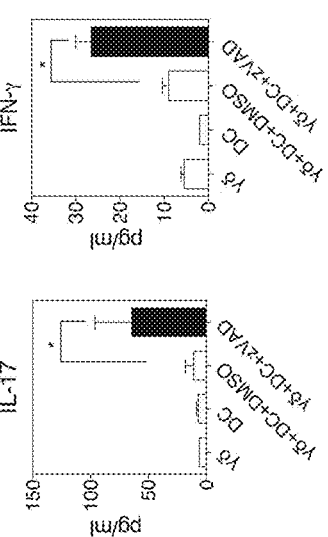

Example 2. Inhibition of Caspase Activity in BMDC Results in Cell Death but Enhanced Ability to Activate γδ T Cells The effect of caspase inhibition on the survival of BMDC was examined. As shown in FIG. 1A, the addition of the pan-caspase blocker zVAD to cultures of BMDC grown in GM-CSF resulted in a substantial amount of cell death within 18 hours that was dose-dependent, yielding nearly 80% dead BMDC at 50 µM zVAD. By contrast, γδ T cells cultured in the same 50 µM dose of zVAD manifested no increase in cell death (FIG. 1A). Despite the augmented cell death of BMDC with zVAD, their ability to activate γδ T cells was considerably enhanced in the presence of B. burgdorferi, as indicated by the augmented production of IL-17 and IFN-γ by the γδ T cells, and their increased expression of surface CD25 (FIG. 1B). In fact, even in the absence of Borrelia, zVAD treatment of BMDC was able to promote some production of IL-17 and IFNγ by γδ T cells, albeit less than in the presence of Borrelia (FIG. 1C). This suggested that inhibition of caspase activity in BMDC resulted in the induction or exposure of a self-antigen that could activate the γδ T cells (data not shown).

Figures 2A, 2B:
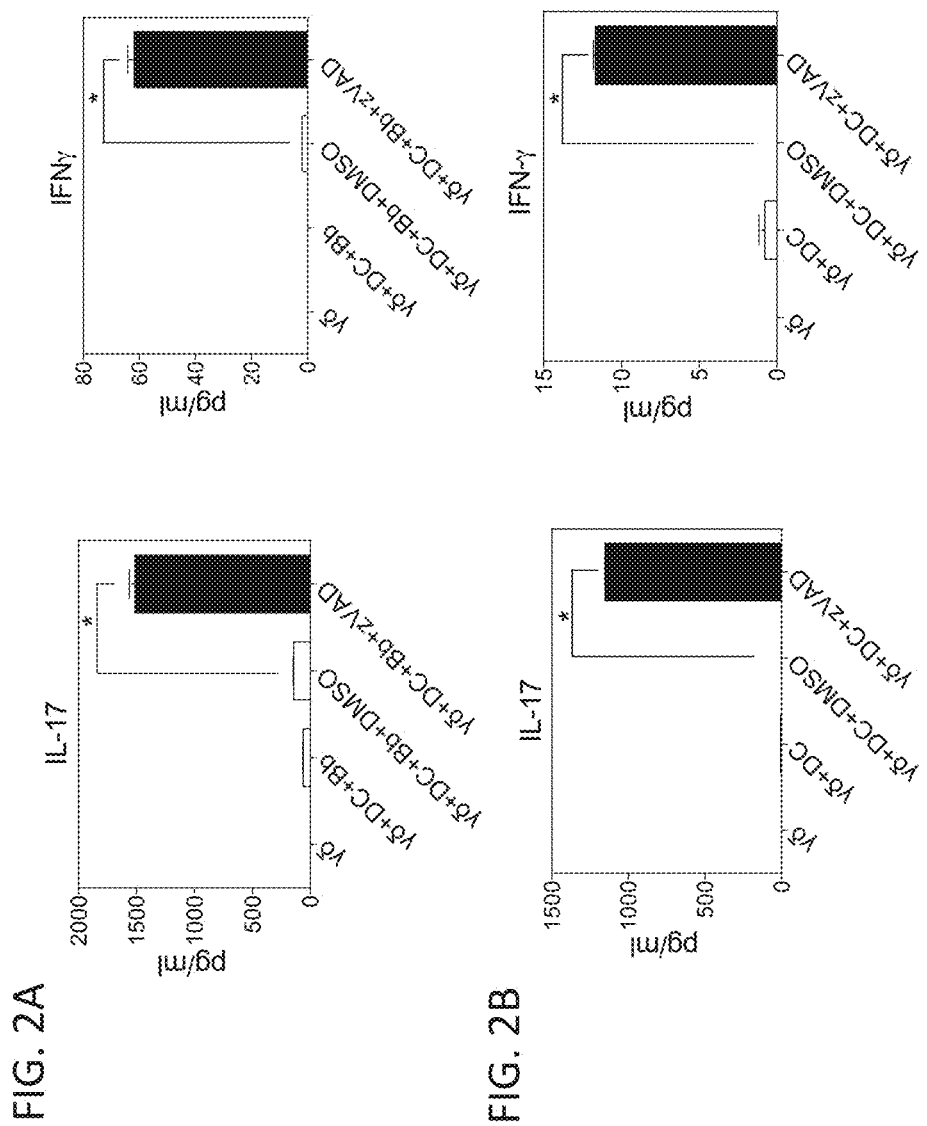
FIGS. 2A-2B show that the caspase inhibition of BMDC also activates freshly isolated murine γδ T cells. Freshly isolated splenic γδ T cells and DC were cultured separately or together at a 1:1 ratio in the (FIG. 2A) presence or (FIG. 2B) absence of B. burgdorferi sonicate (Bb) (10 μg/ml). Either zVAD (50 μM) or control DMSO was added to cultures as indicated. After 20 h, supernatants were assessed for production of the γδ T cell cytokines IL-17 and IFN-γ by Luminex assay (*$p<0.05$ by one-way ANOVA followed by Tukey's post-test). Data represent triplicate wells from one of two experiments.

Freshly isolated splenic γδ T cells behaved similarly to cultured γδ T cells. In the presence of zVAD-treated DC and Borrelia, fresh γδ T cells greatly augmented production IL-17 and IFN-γ (FIG. 2A), and this occurred even in the absence of Borrelia (FIG. 2B).

To further investigate how zVAD-treated BMDC might activate γδ T cells, whether the process involved a soluble factor or direct cell-to-cell contact was examined. Initial examination of cytokine production by the BMDC revealed that zVAD did not augment, and actually partially inhibited, the production of IL-12 p40 or p70 by Borrelia-stimulated BMDC (FIG. 3A). BMDC production of IL-1β, which requires caspase-1 to cleave it into an active form, was completely inhibited by zVAD. By contrast, BMDC production of TNF-α was augmented in the presence of zVAD. In addition, blocking of IL-1β, IL-12, IL-18, or all three did not affect the activation of γδ T cells, as defined by their production of IL-17 or IFN-γ (FIG. 3B). Moreover, the addition of these cytokines, individually or in combination, did not augment γδ T cell activation. However, blocking of TNF-α substantially reduced the production of IFN-γ, but not IL-17, by the γδ T cells (FIG. 3C). In addition, the addition of TNF-α to cultures, in the absence of Borrelia, did not augment production of either IL-17 or IFNγ. Consistent with these findings, use of BMDC from TNF-α$^{-/-}$ mice only partly reduced the activation of γδ seen with wild-type BMDC+Borrelia (FIG. 3D). These findings suggested that a factor in addition to TNF-α was produced by BMDC+zVAD that could activate γδ T cells.

Figure 4A:
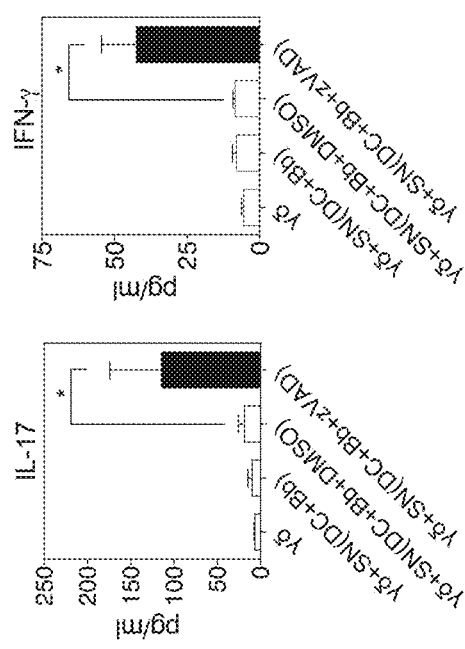
FIGS. 4A-4B show that the augmented activation of γδ T cells by caspase-inhibited BMDC involves a soluble factor.
Figure 4B:
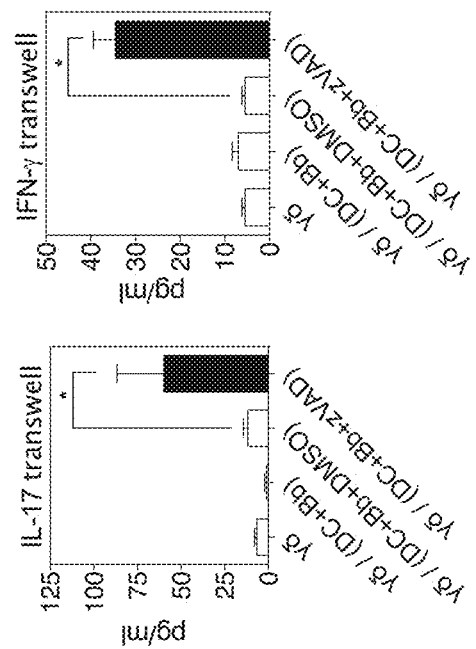

Further analyses suggested that the factor(s) activating the γδ T cells was soluble. First, supernatants alone from cultures containing γδ T cells plus BMDC+Borrelia+zVAD, could augment activation of the γδ T cells in the absence of added BMDC or Borrelia (FIG. 4A). In addition, transwell assays revealed that in the absence of cell contact between the BMDC and γδ T cells, there was still partial activation of γδ T cells in the presence of BMDC+Borrelia+zVAD (FIG. 4B). In addition to soluble cytokines secreted by BMDC, it is also possible that a ligand(s) for the γδ T cells was induced or exposed by the BMDC during the stress induced by caspase inhibition that could pass the restriction size (0.4 µm) of the transwell system. This further suggests that the ligand(s) for TCR-γδ did not require cell surface presentation as with TCR-αβ.

Figure 5:
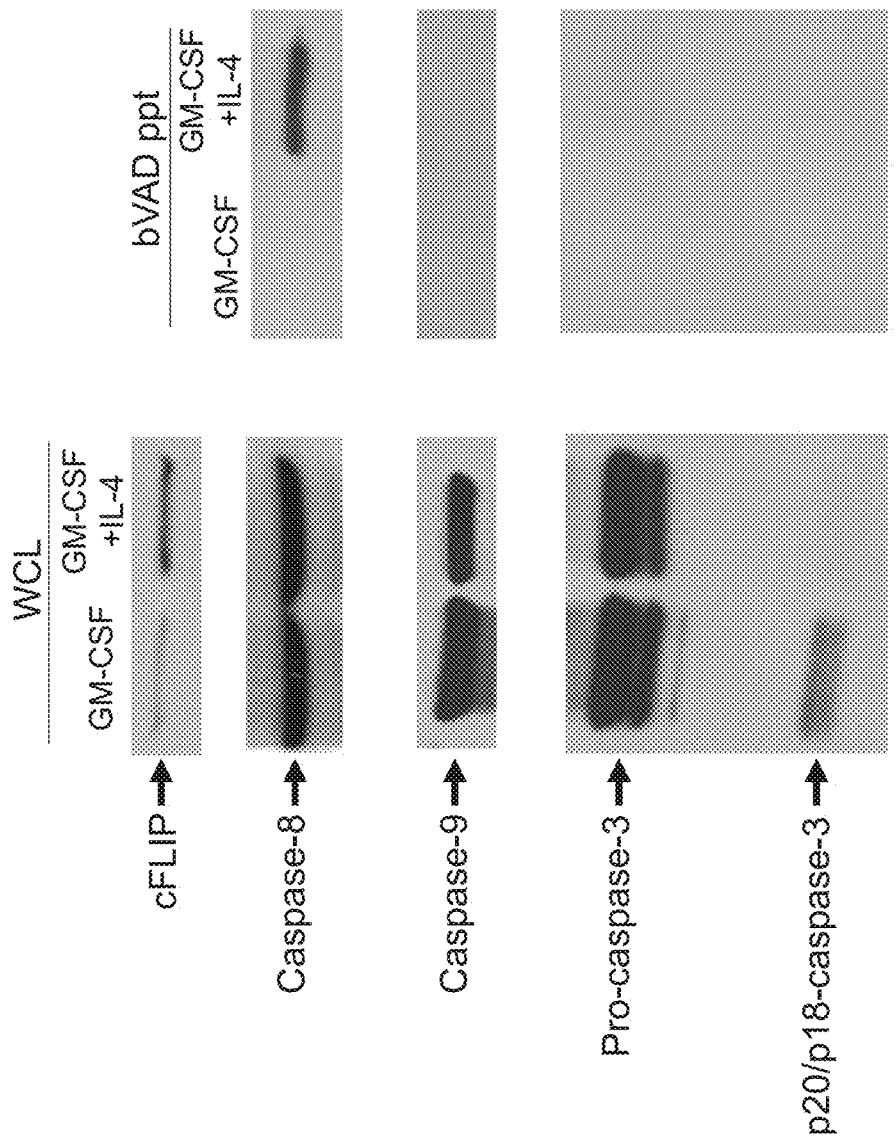
FIG. 5 demonstrates that IL-4 induces c-FLIP and caspase-8 activity in BMDC. BMDC were cultivated in GM-CSF in the absence or presence of IL-4. After 7 days, lysates were made containing biotin-VAD (bVAD) to bind active caspases. Active caspases were then selectively precipitated using avidin-sepharose (bVAD ppt) and compared to whole cell lysates (WCL) by immunoblot for c-FLIP, caspase-8, caspase-9, and caspase-3. The results were consistent in two experiments.

Example 3. Caspase-8 Activity is Detectable in BMDC and is Increased by IL-4 Induction of c-FLIP The levels of specific caspases and their degree of activity using biotin-VAD (bVAD) to selectively bind only the active caspase fraction, which was then precipitated with avidin-sepharose were examined. In addition, the levels of the caspase-8 paralogue c-FLIP, which regulates the level of caspase-8 activity were monitored. Although c-FLIP was originally described as a competitive inhibitor of caspase-8 following Fas-induced cell death (28), subsequent studies revealed that it is also an activator of moderate caspase-8 activity, which is essential for cell survival (23, 29). In addition, it has been observed that c-FLIP levels increase during the maturation of DC in the presence of IL-4 (10, 24-26). As shown in FIG. 5, there was no difference in the levels of total cellular caspase-8, caspase-9, or caspase-3 in whole cell lysates from BMDC grown in GM-CSF or GM-CSF+IL-4. However, IL-4 considerably increased the level of c-FLIP (FIG. 5). This paralleled an increase in the level of active caspase-8 in BMDC cultured in GM-CSF+IL-4 (FIG. 5). However, active caspase-9 and caspase-3 were undetectable in bVAD precipitates, even at long exposures (FIG. 5). Thus, the active caspase-8 signal did not propagate to downstream caspases.

Cell death resulting from the absence of caspase-8 or FADD can be rescued by the loss of RIPK3 or RIPK1 (19, 30). Caspase-8 activity is required in proliferating cells to cleave RIPK1, which prevents the formation of the Ripoptosome and subsequent cell death by necroptosis (31). Consistent with this model, BMDC exhibited cleaved RIPK1 in both growth conditions (FIG. 6A). However, the addition of zVAD completely inhibited cleavage of RIPK1 in BMDC cultured with GM-CSF only, whereas in the presence of GM-CSF+IL-4, zVAD only partially inhibited RIPK1 cleavage. This is consistent with both the increased caspase-8 activity in these cells as well as the known ability of c-FLIP to reduce accessibility of zVAD to the enzymatic pocket of caspase-8. The persistence of cleaved RIPK1 despite zVAD in GM-CSF+IL-4-cultured BMDC was paralleled by greatly reduced cell death in the presence of zVAD compared to BMDC cultured with only GM-CSF (FIG. 6B).

Given these findings the RIPK1 inhibitor, Necrostatin (32), was used to examine whether RIPK1 activity influenced either cell death mediated by zVAD, or the ability of zVAD-treated BMDC to augment γδ T cell stimulation. Addition of Necrostatin to GM-CSF-cultured BMDC treated with zVAD rescued them from cell death (FIG. 6C). Furthermore, Necrostatin also reversed the ability of zVAD-treated BMDC to produce TNF-α or to augment activation of γδ T cells, as defined by production of IL-17 and IFN-γ (FIG. 6D). Necrostatin was not simply toxic to the cells as it did not block production of these cytokines with *Borrelia* in the absence of zVAD (FIG. 6D). Thus, RIPK1-mediated necroptosis of BMDC enhanced γδ T cell activation.

Example 4. IL-4 Reduces the Ability of zVAD-Treated BMDC to Activate γδ T Cells

Although zVAD treatment of GM-CSF-cultured BMDC augmented their ability to activate γδ T cells, it was not certain that this was due to reduced caspase activity and cell death. BMDC cultured with GM-CSF+IL-4 afforded an opportunity to test this, given their greater caspase-8 activity and resistance to zVAD-induced cell death. In fact BMDC grown with GM-CSF+IL-4 were much less able to activate *Borrelia*-stimulated γδ T cells in either the absence or presence of zVAD (FIG. 7). This supports the view that the actual cell stress or death caused by caspase inhibition of BMDC was responsible for the induction of a factor(s) that could promote activation of γδ T cells.

Figure 8A:
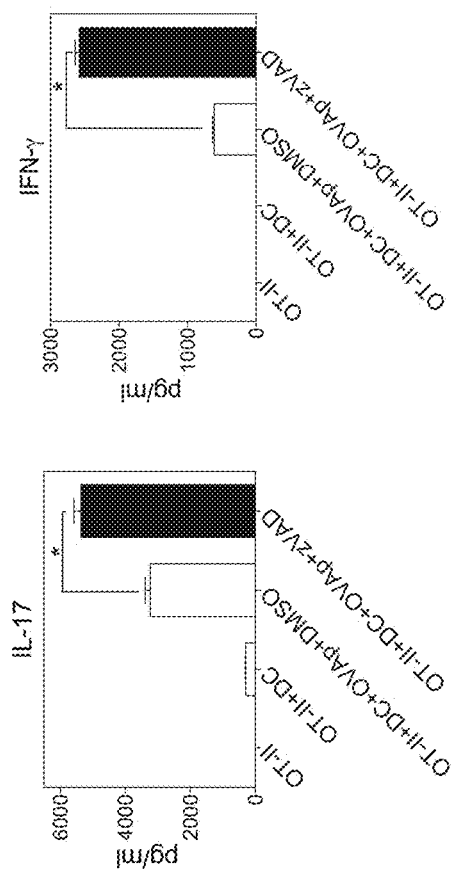
FIGS. 8A-8C show that caspase inhibition of BMDC also promotes activation of murine αβ and human γδ T cells.
Figure 8C:
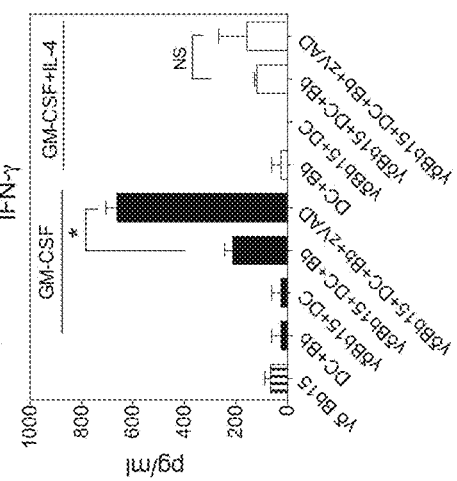
Figure 8B:
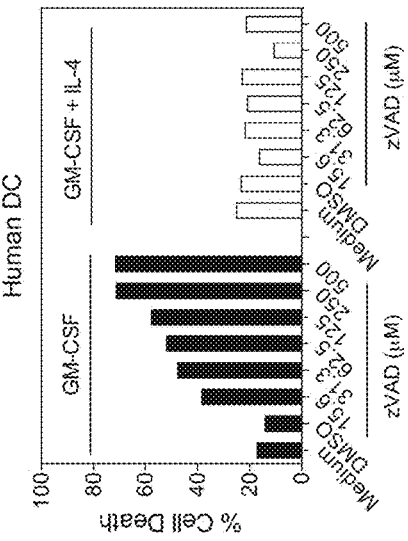

Example 5. Necroptosis of DC Also Enhances Activation of Fresh Antigen-Specific αβ T Cells, as Well As Human γδ T Cells The observations using murine γδ T cells were further examined to determine if they were more broadly applicable to antigen-activated αβ T cells. Freshly isolated CD4⁻ αβ OT-II T cells were activated with ovalbumin peptide (OVAp) and DC that were treated or not with zVAD (50 μM). As shown in FIG. 8A, zVAD-treatment of DC considerably augmented the production of IL-17 and IFN-γ by OT-II T cells. Unlike the γδ T cells, however, no cytokine production was induced without the addition of antigen OVAp (data not shown). The ability of necroptotic DC to augment γδ T cell activation also extended to human γδ T cells. Human DC from peripheral blood monocytes cultured with GM-CSF were highly susceptible to death with zVAD at doses very similar to murine DC, and this was also blocked by the addition of IL-4 (FIG. 8B). We further examined the ability of zVAD-treated human DC to promote activation of human *Borrelia*-reactive synovial γδ T cell clones from Lyme arthritis (8). FIG. 8C shows an example for one of three synovial Vδ1 clones examined, Bb15, revealing increased IFN-γ production (the synovial γδ T cell clones do not produce IL-17) when cultured with *Borrelia* plus zVAD-treated DC cultured with GM-CSF alone, but not when cultured with IL-4. These findings establish the ability of necroptotic DC to augment T cell immune responses.

Discussion

Thus, the findings of the invention support a model in which murine and human γδ T cells respond to cells dying by necroptosis, consistent with the notion that γδ T cells function in a stress-surveillance immune response. This study further extends to BMDC the growing list of cells that have been shown to require caspase activity for survival. Additionally, the findings demonstrate that IL-4-induced upregulation of the caspase-8 paralogue, c-FLIP, parallels an increase in caspase-8 activity in BMDC. This is consistent with the ability of c-FLIP to activate caspase-8 in its full-length form (23). IL-4-induced c-FLIP also reduces the ability of BMDC to activate γδ T cells, even in the presence of zVAD. As such, c-FLIP expression may be central to the regulation of inflammatory versus tolerogenic DC function. These mice had reduced numbers of DC, consistent with the requirement of c-FLIP for their survival. Of particualr interest was that these mice spontaneously developed autoreactive CD4⁺ T cells and inflammatory arthritis.

Very few ligands are known for murine or human γδ T cells. The MHC class I-like molecule T22 is recognized by the murine γδ T cell clone G8, almost exclusively through the δ-chain (36). By contrast, Endothelial Protein C Receptor was recently shown to be a ligand for a human γδ T cell clone from a CMV-infected individual, largely through the γ-chain (37). The stress-inducible MHC class I-like molecules MICA in humans (38) and Rae-1 in the mouse (39) engage the activating receptor NKG2D, found on most γδ T cells (38, 40), as well as engaging some TCR-γδ (40). CD1d complexed with sulfatide was also recently reported to be a ligand for some human γδ T cells (41). In addition, phosphoantigens from infectious agents alkylamies can activate certain human but not murine γδ T cells (42-44). Many of these potential ligands are induced during infections or various types of cell stress. This has proffered the notion that γδ T cells are inherently biased toward the recognition of autologous molecules during cell stress or death (2). The previous findings of the γδ T cell response to *Borrelia* are consistent with this view. It was found that both murine and human γδ T cells respond to *Borrelia* indirectly in a TLR2-dependent manner (9). It is of interest to note that *Borrelia* has been reported to also induce cell death of monocytes (12). A soluble human TCR-γδ tetramer derived from a Lyme arthritis synovial γδ T cell clone has been observed to react particularly well with intracellular components of *Borrelia*-stimulated monocytes (C.C., unpublished observations). Collectively these findings support a model in which γδ T cells respond to infection- or stress-induced cellular self-components.

Since the initial description that caspase-8 activity is required for T cell proliferation (13), a growing list of cell types has been identified that require caspase-8 activity for cell survival and growth (13-17). This includes endothelial cells, bone marrow cells, and hepatocytes, among others (16). It has become of considerable interest how caspase-8 activity is regulated between the modest levels in membrane lipid rafts that are required for cell growth versus the large cytoplasmic levels of active caspase-8 initiated following engagement of cell death receptors such as Fas (CD95) (45, 46). The caspase-8 paralogue, c-FLIP, has been observed to be a critical regulator of caspase-8 activity (23, 47). c-FLIP can inhibit caspase-8 activation via Fas by competing with caspase-8 for recruitment to FADD in the death-inducing signal complex (28, 48). Paradoxically, c-FLIP can also heterodimerize with caspase-8 independently of death receptor engagement, in which case c-FLIP provides activation of full-length caspase-8 during cell growth (23). The lower level of caspase-8 activity was observed in BMDC grown with only GM-CSF likely reflected the reduced levels of c-FLIP, as it was observed that deletion of c-FLIP in T cells or mouse embryonic fibroblasts results in loss of active caspase-8 (49), whereas increased c-FLIP augments caspase-8 activity (47). It has recently been appreciated that caspase-8 activity is required to maintain cleavage of RIPK1 (20, 22). In the absence of active caspase-8, full-length RIPK1 can form a complex known as the Ripoptosome, which induces a caspase-independent cell death or necroptosis (21, 22). Thus, c-FLIP emerges as a key regulator of the Ripoptosome. Activation of the Ripoptosome has also recently been linked to activation of the Inflammasome (48). Hence, the production of the endogenous self-ligand(s) recognized by γδ T cells may occur through activation of the Ripoptosome and the Inflammasome. Future studies will determine to what extent c-FLIP and caspase-8 levels differ in various in vivo DC subsets, as well as their susceptibility to zVAD-mediated cell death.

The finding that IL-4 upregulates c-FLIP in DC adds a new dimension to the known ability of IL-4 to promote "alternate activation" of M2 macrophages (51). Classically activated M1 macrophages, following exposure to IFN-γ, acquire tumoricidal activity and can elicit tissue-destructive reactions. By contrast, IL-4 and IL-13 can induce alternative activation of M2 macrophages that are oriented more toward tissue repair and remodeling, immunoregulation, and tumor promotion (52). This is accompanied by upregulation of the mannose receptor, certain chemokines such as CCL22, and intracellular enzymes such as arginase, which are implicated in cell recruitment and granuloma formation (52). We found that the increased expression of c-FLIP in DC with IL-4 paralleled increased caspase-8 activity and hence resistance to zVAD-induced cell death. c-FLIP can also inhibit Fas-mediated cell death and divert signals toward the NF-κB and ERK pathways, by virtue of the ability of c-FLIP to associate with TRAF2 and Raf-1. The current findings reveal the ability of necroptotic DC to augment activation of T cells and to upregulate ligands for γδ T cells, underscoring their role in the immune surveillance of cell stress.

REFERENCES

1. Born, W., C. Cady, J. Jones-Carson, A. Mukasa, M. Lahn, and R. O'Brien. 1999. Immunoregulatory functions of gamma delta T cells. *Adv. Immunol.* 71: 77-144.
2. Kalyan, S., and D. Kabelitz. 2013. Defining the nature of human T cells: a biographical sketch of the highly empathetic. *Cell. Mol. Immunol.* 10: 21-29.
3. Vantourout, P., and A. Hayday. 2013. Six-of-the-best: unique contributions of T cells to immunology. *Nat. Rev. Immunol.* 13: 88-100.
4. Brennan, F. M., M. Londei, A. M. Jackson, T. Hercend, M. B. Brenner, R. N. Maini, and M. Feldmann. 1988. T cells expressing gamma delta chain receptors in rheumatoid arthritis. *J. Autoimmun.* 1: 319-326.
5. Vincent, M., K. Roessner, D. Lynch, S. M. Cooper, L. H. Sigal, and R. C. Budd. 1996. Apoptosis of Fas high CD4+ Synovial T cells by *Borrelia* reactive Fas Ligand high gamma delta T cells in Lyme Arthritis. J. Exp. Med. 184: 2109-2117.
6. Rust, C., Y. Kooy, S. Pena, M. L. Mearin, P. Kluin, and F. Koning. 1992. Phenotypical and functional characterization of small intestinal TcR gamma delta+ T cells in coeliac disease. Scand. J. Immunol. 35: 459-468.
7. Balbi, B., D. R. Moller, M. Kirby, K. J. Holroyd, and R. G. Crystal. 1990. Increased numbers of T lymphocytes with gamma delta-positive antigen receptors in a subgroup of individuals with pulmonary sarcoidosis. *J. Clin. Invest.* 85: 1353-1361.
8. Vincent, M. S., K. Roessner, T. Sellati, C. D. Huston, L. H. Sigal, S. M. Behar, J. D. Radolf, and R. C. Budd. 1998. Lyme arthritis synovial gamma delta T cells respond to *Borrelia burgdorferi* lipoproteins and lipidated hexapeptides. *J. Immunol.* 161: 5762-5771.
9. Collins, C., C. Shi, J. Q. Russell, K. A. Fortner, and R. C. Budd. 2008. Activation of gammadelta T cells by *Borrelia burgdorferi* is indirect via a TLR- and caspase-dependent pathway. J. Immunol. 181: 2392-2398.
10. Collins, C., J. Wolfe, K. Roessner, C. Shi, L. H. Sigal, and R. C. Budd. 2005. Lyme arthritis synovial gammadelta T cells instruct dendritic cells via fas ligand. J. Immunol. 175: 5656-5665.
11. Shi, C., B. Sahay, J. Q. Russell, K. A. Fortner, N. Hardin, T. J. Sellati, and R. C. Budd. 2011. Reduced immune response to *Borrelia burgdorferi* in the absence of γδ T cells. *Infect. Immun.* 79: 3940-3946.
12. Cruz, A. R., M. W. Moore, C. J. La Vake, C. H. Eggers, J. C. Salazar, and J. D. Radolf. 2008. Phagocytosis of *Borrelia burgdorferi*, the Lyme disease spirochete, potentiates innate immune activation and induces apoptosis in human monocytes. *Infect. Immun.* 76: 56-70.
13. Kennedy, N. J., T. Kataoka, J. Tschopp, and R. C. Budd. 1999. Caspase activation is required for T cell proliferation. *J. Exp. Med.* 190: 1891-1896.
14. Chun, H. J., L. Zheng, M. Ahmad, J. Wang, C. K. Speirs, R. M. Siegel, J. K. Dale, J. Puck, J. Davis, C. G. Hall, S. Skoda-Smith, T. P. Atkinson, S. E. Straus, and M. J. Lenardo. 2002. Pleiotropic defects in lymphocyte activation caused by caspase-8 mutations lead to human immunodeficiency. Nature 419: 395-399.
15. Salmena, L., B. Lemmers, A. Hakem, E. Matysiak-Zablocki, K. Murakami, P. Y. Au, D. M. Berry, L. Tamblyn, A. Shehabeldin, E. Migon, A. Wakeham, D. Bouchard, W. C. Yeh, J. C. McGlade, P. S. Ohashi, and R. Hakem. 2003. Essential role for caspase 8 in T-cell homeostasis and T-cell-mediated immunity. *Genes Dev.* 17: 883-895.
16. Kang, T. B., T. Ben-Moshe, E. E. Varfolomeev, Y. Pewzner-Jung, N. Yogev, A. Jurewicz, A. Waisman, O. Brenner, R. Haffner, E. Gustafsson, P. Ramakrishnan, T. Lapidot, and D. Wallach. 2004. Caspase-8 serves both apoptotic and nonapoptotic roles. *J. Immunol.* 173: 2976-2984.
17. Helfer, B., B. C. Boswell, D. Finlay, A. Cipres, K. Vuori, T. Bong Kang, D. Wallach, A. Dorfleutner, J. M. Lahti, D. C. Flynn, and S. M. Frisch. 2006. Caspase-8 promotes cell motility and calpain activity under nonapoptotic conditions. *Cancer Res.* 66: 4273-4278.
18. Varfolomeev, E. E., M. Schuchmann, V. Luria, N. Chiannilkulchai, J. S. Beckmann, I. L. Mett, D. Rebrikov, V. M. Brodianski, O. C. Kemper, O. Kollet, T. Lapidot, D. Soffer, T. Sobe, K. B. Avraham, T. Goncharov, H. Holtmann, P. Lonai, and D. Wallach. 1998. Targeted disruption of the mouse Caspase 8 gene ablates cell death induction by the TNF receptors, Fas/Apol, and DR3 and is lethal prenatally. *Immunity* 9: 267-276.

19. Kaiser, W. J., J. W. Upton, A. B. Long, D. Livingston-Rosanoff, L. P. Daley-Bauer, R. Hakem, T. Caspary, and E. S. Mocarski. 2011. RIP3 mediates the embryonic lethality of caspase-8-deficient mice. *Nature* 471: 368-372.
20. Zhang, H., X. Zhou, T. McQuade, J. Li, F. K. Chan, and J. Zhang. 2011. Functional complementation between FADD and RIP1 in embryos and lymphocytes. *Nature* 471: 373-376.
21. Feoktistova, M., P. Geserick, B. Kellert, D. P. Dimitrova, C. Langlais, M. Hupe, K. Cain, M. MacFarlane, G. Hacker, and M. Leverkus. 2011. cIAPs block Ripoptosome formation, a RIP1/caspase-8 containing intracellular cell death complex differentially regulated by cFLIP isoforms. *Mol. Cell* 43: 449-463.
22. Tenev, T., K. Bianchi, M. Darding, M. Broemer, C. Langlais, F. Wallberg, A. Zachariou, J. Lopez, M. MacFarlane, K. Cain, and P. Meier. 2011. The Ripoptosome, a signaling platform that assembles in response to genotoxic stress and loss of IAPB. *Mol. Cell* 43: 432-448.
23. Micheau, O., M. Thome, P. Schneider, N. Holler, J. Tschopp, D. W. Nicholson, C. Briand, and M. G. Grutter. 2002. The long form of FLIP is an activator of caspase-8 at the Fas death-inducing signaling complex. *J. Biol. Chem.* 277: 45162-45171.
24. Rescigno, M., V. Piguet, B. Valzasina, S. Lens, R. Zubler, L. French, V. Kindler, J. Tschopp, and P. Ricciardi-Castagnoli. 2000. Fas engagement induces the maturation of dendritic cells (DCs), the release of interleukin (IL)-1beta, and the production of interferon gamma in the absence of IL-12 during DC-T cell cognate interaction. A new role for fas ligand in inflammatory responses. *J. Exp. Med.* 192: 1661-1668.
25. Perlman, H., L. J. Pagliari, H. Liu, A. E. Koch, G. K. Haines, 3rd, and R. M. Pope. 2001. Rheumatoid arthritis synovial macrophages express the Fas-associated death domain-like interleukin-1beta-converting enzyme-inhibitory protein and are refractory to Fas-mediated apoptosis. *Arthritis Rheum.* 44: 21-30.
26. Ashany, D., A. Savir, N. Bhardwaj, and K. B. Elkon. 1999. Dendritic cells are resistant to apoptosis through the Fas (CD95/APO-1) pathway. *J. Immunol.* 163: 5303-5311.
27. Barnden, M. J., J. Allison, W. R. Heath, and F. R. Carbone. 1998. Defective TCR expression in transgenic mice constructed using cDNA-based alpha- and beta-chain genes under the control of heterologous regulatory elements. *Immunol. Cell Biol.* 76: 34-40.
28. Irmler, M., M. Thome, M. Hahne, P. Schneider, K. Hofmann, V. Steiner, J. L. Bodmer, M. Schroter, K. Burns, C. Mattmann, D. Rimoldi, L. E. French, and J. Tschopp. 1997. Inhibition of death receptor signals by cellular FLIP. *Nature* 388: 190-195.
29. Yeh, W. C., A. Itie, A. J. Elia, M. Ng, H. B. Shu, A. Wakeham, C. Mirtsos, N. Suzuki, M. Bonnard, D. V. Goeddel, and T. W. Mak. 2000. Requirement for Casper (c-FLIP) in regulation of death receptor-induced apoptosis and embryonic development. *Immunity* 12: 633-642.
30. Oberst, A., C. P. Dillon, R. Weinlich, L. L. McCormick, P. Fitzgerald, C. Pop, R. Hakem, G. S. Salvesen, and D. R. Green. 2011. Catalytic activity of the caspase-8-FLIP (L) complex inhibits RIPK3-dependent necrosis. *Nature* 471: 363-367.
31. Feoktistova, M., P. Geserick, B. Kellert, D. P. Dimitrova, C. Langlais, M. Hupe, K. Cain, M. MacFarlane, G. Hacker, and M. Leverkus. cIAPs block Ripoptosome formation, a RIP1/caspase-8 containing intracellular cell death complex differentially regulated by cFLIP isoforms. *Mol. Cell* 43: 449-463.
32. Boatright, K. M., C. Deis, J. B. Denault, D. P. Sutherlin, and G. S. Salvesen. 2004. Activation of caspases-8 and -10 by FLIP(L). Biochem J382: 651-657.
33. McStay, G. P., G. S. Salvesen, and D. R. Green. 2008. Overlapping cleavage motif selectivity of caspases: implications for analysis of apoptotic pathways. *Cell Death Diff.* 15: 322-331.
34. Linkermann, A., J. H. Brasen, F. De Zen, R. Weinlich, R. A. Schwendener, D. R. Green, U. Kunzendorf, and S. Krautwald. 2012. Dichotomy between RIP1- and RIP3-mediated necroptosis in tumor necrosis factor-alpha-induced shock. *Mol. Med.* 18: 577-586.
35. Huang, Q. Q., H. Perlman, R. Birkett, R. Doyle, D. Fang, G. K. Haines, W. Robinson, S. Datta, Z. Huang, Q. Z. Li, H. Phee, and R. M. Pope. 2015. CD11c-mediated deletion of Flip promotes autoreactivity and inflammatory arthritis. *Nature Com.* 6: 7086.
36. Adams, E. J., Y. H. Chien, and K. C. Garcia. 2005. Structure of a gammadelta T cell receptor in complex with the nonclassical MHC T22. *Science* 308: 227-231.
37. Willcox, C. R., Pitard, V., Netzer, S., Couzi, L., Salim, M., Silberzahn, T., Moreau, J-F., Hayday, A. C., Willcox, B. E., Dechanet-Merville, J. 2012. Cytomegalovirus and tumor stress surveillance by binding of a human gamma delta T cell antigen receptor to endothelial protein C receptor. *Nat. Immunol.* 13: 872-880.
38. Bauer, S., V. Groh, J. Wu, A. Steinle, J. H. Phillips, L. L. Lanier, and T. Spies. 1999. Activation of NK cells and T cells by NKG2D, a receptor for stress-inducible MICA. *Science* 285: 727-729.
39. Girardi, M., D. E. Oppenheim, C. R. Steele, J. M. Lewis, E. Glusac, R. Filler, P. Hobby, B. Sutton, R. E. Tigelaar, and A. C. Hayday. 2001. Regulation of cutaneous malignancy by gammadelta T cells. *Science* 294: 605-609.
40. Xu, B., J. C. Pizarro, M. A. Holmes, C. McBeth, V. Groh, T. Spies, and R. K. Strong. 2011. Crystal structure of a gammadelta T-cell receptor specific for the human MEW class I homolog MICA. *Proc. Nat. Acad. Sci.* 108: 2414-2419.
41. Luoma, A. M., C. D. Castro, T. Mayassi, L. A. Bembinster, L. Bai, D. Picard, B. Anderson, L. Scharf, J. E. Kung, L. V. Sibener, P. B. Savage, B. Jabri, A. Bendelac, and E. J. Adams. 2013. Crystal structure of V1 T cell receptor in complex with CD1d-sulfatide shows MHC-like recognition of a self-lipid by human T cells. *Immunity* 39: 1032-1042.
42. Dieli, F., D. Vermijlen, F. Fulfaro, N. Caccamo, S. Meraviglia, G. Cicero, A. Roberts, S. Buccheri, M. D'Asaro, N. Gebbia, A. Salerno, M. Eberl, and A. C. Hayday. 2007. Targeting human {gamma}delta} T cells with zoledronate and interleukin-2 for immunotherapy of hormone-refractory prostate cancer. *Cancer Res.* 67: 7450-7457.
43. Champagne, E. 2011. gammadelta T cell receptor ligands and modes of antigen recognition. *Archiv. Immunol. Ther. Exp.* 59: 117-137.
44. Bukowski, J. F., C. T. Morita, and M. B. Brenner. 1999. Human gamma delta T cells recognize alkylamines derived from microbes, edible plants, and tea: implications for innate immunity. *Immunity* 11: 57-65.
45. Su, H., N. Bidere, L. Zheng, A. Cubre, K. Sakai, J. Dale, L. Salmena, R. Hakem, S. Straus, and M. Lenardo. 2005. Requirement for caspase-8 in NF-kappaB activation by antigen receptor. *Science* 307: 1465-1468.

46. Misra, R. S., J. Q. Russell, A. Koenig, J. A. Hinshaw-Makepeace, R. Wen, D. Wang, H. Huo, D. R. Littman, U. Ferch, J. Ruland, M. Thome, and R. C. Budd. 2007. Caspase-8 and c-FLIPL associate in lipid rafts with NF-kappaB adaptors during T cell activation. *J. Biol. Chem.* 282: 19365-19374.

47. Dohrman, A., J. Q. Russell, S. Cuenin, K. Fortner, J. Tschopp, and R. C. Budd. 2005. Cellular FLIP Long Form Augments Caspase Activity and Death of T Cells through Heterodimerization with and Activation of Caspase-8. *J. Immunol.* 175: 311-318.

48. Thome, M., P. Schneider, K. Hofmann, H. Fickenscher, E. Meinl, F. Neipel, C. Mattmann, K. Burns, J.-L. Bodmer, M. Schroter, C. Scaffidi, P. H. Krammer, M. E. Peter, and J. Tschopp. 1997. Viral FLICE-inhibitory proteins (FLIPs) prevent apoptosis induced by death receptors. *Nature* 386: 517-520.

49. Koenig, A., I. A. Buskiewicz, K. A. Fortner, J. Q. Russell, T. Asaoka, Y. W. He, R. Hakem, J. E. Eriksson, and R. C. Budd. 2014. The c-FLIPL cleavage product p43FLIP promotes activation of extracellular signal-regulated kinase (ERK), nuclear factor B (NF-B), and caspase-8 and T cell survival. *J. Biol. Chem.* 289: 1183-1191.

50. Vince, J. E., W. W. Wong, I. Gentle, K. E. Lawlor, R. Allam, L. O'Reilly, K. Mason, O. Gross, S. Ma, G. Guarda, H. Anderton, R. Castillo, G. Hacker, J. Silke, and J. Tschopp. 2012. Inhibitor of apoptosis proteins limit RIP3 kinase-dependent interleukin-1 activation. *Immunity* 36: 215-227.

51. Ma, J., T. Chen, J. Mandelin, A. Ceponis, N. E. Miller, M. Hukkanen, G. F. Ma, and Y. T. Konttinen. 2003. Regulation of macrophage activation. *Cell. Mol. Life Sci.* 60: 2334-2346.

52. Gordon, S., and F. O. Martinez. 2010. Alternative activation of macrophages: mechanism and functions. *Immunity* 32: 593-604.

53. Kataoka, T., R. C. Budd, N. Holler, M. Thome, F. Martinon, M. Irmler, K. Burns, M. Hahne, N. Kennedy, M. Kovacsovics, and J. Tschopp. 2000. The caspase-8 inhibitor FLIP promotes activation of NF-kappaB and Erk signaling pathways. *Curr. Biol.* 10: 640-648.

54. Kataoka, T., and J. Tschopp. 2004. N-Terminal Fragment of c-FLIP(L) Processed by Caspase 8 Specifically Interacts with TRAF2 and Induces Activation of the NF-κB Signaling Pathway. *Mol. Cell. Biol.* 24: 2627-2636.

55. Dohrman, A., T. Kataoka, S. Cuenin, J. Q. Russell, J. Tschopp, and R. C. Budd. 2005. Cellular FLIP (long form) regulates CD8+ T cell activation through caspase-8-dependent NF-kappa B activation. *J. Immunol.* 174: 5270-5278.

56. Qian, C., L. Qian, Y. Yu, H. An, Z. Guo, Y. Han, Y. Chen, Y. Bai, Q. Wang, and X. Cao. 2013. Fas signal promotes the immunosuppressive function of regulatory dendritic cells via the ERK/beta-catenin pathway. *J. Biol. Chem.* 288: 27825-27835.

57. Roessner, K., J. Wolfe, C. Shi, L. H. Sigal, S. Huber, and R. C. Budd. 2003. High expression of Fas ligand by synovial fluid-derived gamma delta T cells in Lyme arthritis. J. Immunol. 170: 2702-2710.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A method for treating cancer in a subject, comprising administering to a subject having cancer a caspase inhibitor and a cancer antigen in an effective amount to treat the cancer.

2. The method of claim 1, wherein the subject has a cancer selected from the group consisting of lymphoma, leukemia, fibrosarcoma, myxosarcoma, liposarcoma, chondrosarcoma, osteogenic sarcoma, chordoma, angiosarcoma, endotheliosarcoma, lymphangiosarconia, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, lung cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

3. The method of claim 1, further comprising administering to the subject an adjuvant.

4. The method of claim 1, wherein the caspase inhibitor is a caspase 8 inhibitor.

5. The method of claim 1, wherein the caspase inhibitor is a pan caspase inhibitor.

6. The method of claim 5, wherein the pan caspase inhibitor is zVAD.

7. The method of claim 1, wherein the caspase inhibitor is an anti-caspase antibody.

8. The method of claim 1, wherein the caspase inhibitor is an inhibitory nucleic acid, and wherein the inhibitory nucleic acid is a small interfering nucleic acid.

9. The method of claim 1, wherein the caspase inhibitor is formulated in a nanoparticle.

* * * * *

SEQUENCE LISTING

<160> NUMBER OF SEQ ID NOS: 1

<210> SEQ ID NO 1
<211> LENGTH: 479
<212> TYPE: PRT
<213> ORGANISM: Homo sapiens

<400> SEQUENCE: 1

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365
```

-continued

```
Ile Pro Val Glu Thr Asp Ser Glu Glu Gln Pro Tyr Leu Glu Met Asp
    370             375             380

Leu Ser Ser Pro Gln Thr Arg Tyr Ile Pro Asp Glu Ala Asp Phe Leu
385             390             395                         400

Leu Gly Met Ala Thr Val Asn Asn Cys Val Ser Tyr Arg Asn Pro Ala
                405             410                     415

Glu Gly Thr Trp Tyr Ile Gln Ser Leu Cys Gln Ser Leu Arg Glu Arg
            420             425             430

Cys Pro Arg Gly Asp Asp Ile Leu Thr Ile Leu Thr Glu Val Asn Tyr
        435             440             445

Glu Val Ser Asn Lys Asp Asp Lys Lys Asn Met Gly Lys Gln Met Pro
    450             455             460

Gln Pro Thr Phe Thr Leu Arg Lys Lys Leu Val Phe Pro Ser Asp
465             470             475
```